United States Patent
Park et al.

(10) Patent No.: US 11,650,204 B2
(45) Date of Patent: May 16, 2023

(54) PLASMO PHOTOELECTRONIC IMMUNOSENSOR

(71) Applicant: THE REGENTS OF THE UNIVERSITY OF MICHIGAN, Ann Arbor, MI (US)

(72) Inventors: Young Geun Park, Ann Arbor, MI (US); Byunghoon Ryu, Ann Arbor, MI (US); Xiaogan Liang, Ann Arbor, MI (US); Katsuo Kurabayashi, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 726 days.

(21) Appl. No.: 16/607,800

(22) PCT Filed: Apr. 23, 2018

(86) PCT No.: PCT/US2018/028856
§ 371 (c)(1),
(2) Date: Oct. 24, 2019

(87) PCT Pub. No.: WO2018/200377
PCT Pub. Date: Nov. 1, 2018

(65) Prior Publication Data
US 2020/0056992 A1 Feb. 20, 2020

Related U.S. Application Data

(60) Provisional application No. 62/489,872, filed on Apr. 25, 2017.

(51) Int. Cl.
*G01N 33/543* (2006.01)
*G01N 21/552* (2014.01)
(Continued)

(52) U.S. Cl.
CPC ..... *G01N 33/54373* (2013.01); *G01N 21/554* (2013.01); *G02B 5/008* (2013.01); *B82Y 15/00* (2013.01); *G01N 2333/715* (2013.01)

(58) Field of Classification Search
CPC ........... G01N 21/554; G01N 33/54373; G01N 2333/715; B82Y 15/00
See application file for complete search history.

(56) References Cited

U.S. PATENT DOCUMENTS

2005/0142565 A1* 6/2005 Samper .............. C12N 15/1003
435/287.2
2005/0255236 A1* 11/2005 Deng ...................... C03C 17/10
428/323
(Continued)

FOREIGN PATENT DOCUMENTS

WO    WO 2016/133899 A1    8/2016

OTHER PUBLICATIONS

Alicea, et al., Non-Abelian statistics and topological quantum information processing in 1D wire networks. Nature Physics 2011, 7 (5), 412-417.
(Continued)

*Primary Examiner* — Melanie Brown
(74) *Attorney, Agent, or Firm* — Casimir Jones, S.C.; Tanya A. Arenson

(57) ABSTRACT

Provided herein are systems and methods for performing assays. In particular, provided herein are systems and methods for performing sensitive and rapid immunoassays.

18 Claims, 19 Drawing Sheets

(51) Int. Cl.
G02B 5/00 (2006.01)
B82Y 15/00 (2011.01)

(56) References Cited

U.S. PATENT DOCUMENTS

| | | | | |
|---|---|---|---|---|
| 2006/0258021 | A1* | 11/2006 | Booksh | B82Y 15/00 427/2.11 |
| 2010/0021910 | A1* | 1/2010 | Cao | C12N 15/1017 435/270 |
| 2011/0014724 | A1* | 1/2011 | Sim | G01N 33/54373 427/337 |
| 2015/0160218 | A1* | 6/2015 | Demirci | C07K 17/14 435/7.37 |
| 2017/0102357 | A1 | 4/2017 | Liang et al. | |
| 2018/0299458 | A1* | 10/2018 | Gerion | G01N 33/74 |
| 2019/0250101 | A1* | 8/2019 | Li | C23C 16/305 |

OTHER PUBLICATIONS

Anupama, K. Chemically and mechanically exfoliated MoS2 for electronic & opto-electronic devices. 2016 Lester Eastman Conference (LEC) IEEE, Aug. 2, 2016, pp. 4-7.
Bhagawati, M. et. al. Quantitative real-time imaging of protein-protein interactions by LSPR detection with micropatterned gold nanoparticles. Anal. Chem., 85, 9564-9571, 2013.
Cant, NE, et al. Surface functionalisation for the self-assembly of nanoparticle/polymer multilayer films. Thin Solid Films 2003; 426: 31-39.
Chen, et al., Multiplex Serum Cytokine Immunoassay Using Nanoplasmonic Biosensor Microarrays. ACS nano 2015, 9 (4), 4173-4181.
Chen, et al., Nanoimprint-Assisted Shear Exfoliation (NASE) for Producing Multilayer MoS2 Structures as Field-Effect Transistor Channel Arrays. ACS Nano, 2015, 9, (9), 8773-8785.
Chen, et al., Stable few-layer MoS2 rectifying diodes formed by plasma-assisted doping. Appl. Phys. Lett., 2013, 103, (14 ), pp. 142110/142111-142110/142114.
Damas, P., et al. Sepsis and serum cytokine concentrations. Crit. Care Med. 25, 405-412 (1997).
Haddada, MB, et al. Optimizing the immobilization of gold nanoparticles on functionalized silicon surfaces: amine- vs thiol-terminated silane. Gold Bull 2013; 46: 335-341.
Haes, et al., A nanoscale optical biosensor: sensitivity and selectivity of an approach based on the localized surface plasmon resonance spectroscopy of triangular silver nanoparticles. J Am Chem. Soc. Sep. 4, 2002; 124(35):10596-604.
Jung et al., Quantitative Interpretation of the Response of Surface Plasmon Resonance Sensors to Adsorbed Films. Langmuir 1998, 14 (19), 5636-5648.
Kokalj, et al., Self-powered Imbibing Microfluidic Pump by Liquid Encapsulation: SIMPLE. Lab on a Chip, 2014, 14, (22), pp. 4329-4333).
Lippitz, B. E. Cytokine patterns in patients with cancer: a systematic review. Lancet Oncol. May 2013;14(6):e218-28.
Liu, M. et al. Double-layer graphene optical modulator. Nano letters 2012, (3), 1482-1485.
Lopez-Sanchez, et al., Ultrasensitive photodetectors based on monolayer MoS2. Nat Nano 2013, 8 (7), 497-501.

Maczynska, I., et al. Proinflammatory cytokine (IL-1beta, IL-6, IL-12, IL-18 and TNF-alpha) levels in sera of patients with subacute cutaneous lupus erythematosus (SCLE). Immunol. Lett. 102, 79-82 (2006).
Mayer, K. et al., A label-free immunoassay based upon localized surface plasmon resonance of gold nanorods. ACS Nano, 2, 687-692, 2008.
McDonnell S. J. et al. Atomically-thin layered films for device applications based upon 2D TMDC materials. Thin Solid Films, vol. 616, Oct. 1, 2016, pp. 482-501.
Miao, J. et al. Surface Plasmon-Enhanced Photodetection in Few Layer MoS2 Phototransistors with Au Nanostructure Arrays, small 2015, 11 (20), 2392-2398.
Nam, et al., MoS2 transistors fabricated via plasma-assisted nanoprinting of few-layer MoS2 flakes into large-area arrays. ACS nano 2013, 7 (7), 5870-5881.
Nam, H. et al. Fabrication and comparison of MoS2 and WSe2 field-effect transistor biosensors. Journal of Vacuum Science & Technology B 2015, 33 (6), 06FG01.
Nam, H. et al. Multiple MoS2 Transistors for Sensing Molecule Interaction Kinetics. Scientific reports 2014, 5, 10546-10546.
Oh et al., Integrated nanoplasmonic sensing for cellular functional immunoanalysis using human blood. ACS nano 2014, 8 (3), 2667-2676.
Oh et al., Multiplexed Nanoplasmonic Temporal Profiling of T-Cell Response under Immunomodulatory Agent Exposure. ACS sensors 2016, 1 (7), 941-948.
Rosman, et.al. Multiplexed plasmon sensor for rapid label-free analyte detection. Nano Lett. 13, 3243-3247, 2013.
Squires, et al., Making it stick: convection, reaction and diffusion in surface-based biosensors. Nature biotechnology, 2008, 26, (4), pp. 417-426.
Su, S. et al. Dual-target electrochemical biosensing based on DNA structural switching on gold nanoparticle-decorated MoS2 nanosheets. ACS applied materials & interfaces 2016, 8 (11), 6826-6833.
Sun, H.; et al. Gold nanoparticle-decorated MoS 2 nanosheets for simultaneous detection of ascorbic acid, dopamine and uric acid. Rsc Advances 2014, 4 (52), 27625-27629.
Tsai, D.-S et al. Few-layer MoS2 with high broadband photogain and fast optical switching for use in harsh environments. Acs Nano 2013, 7 (5), 3905-3911.
Visentainer, J. E. L., et al. Serum cytokine levels and acute graft-versus-host disease after HLA-identical hematopoietic stem cell transplantation. Exp Hematol. Nov. 2003;31(11):1044-50.
Wang X. et al. Ultrasensitive and Broadband MoS2 Photodetector Driven by Ferroelectrics. Adv Mater. Nov. 2015;27(42):6575-81.
Wi et al., High blue-near ultraviolet photodiode response of vertically stacked graphene-MoS2-metal heterostructures. Appl. Phys. Lett., 2014, 104, pp. 232103/232101-232103/23210.
Wi, et al., Enhancement of photovoltaic response in multilayer MoS2 induced by plasma doping. ACS Nano, 2014, 8, (5), pp. 5270-5281.
Wi, et al., Photovoltaic response in pristine WSe2 layers modulated by metal-induced surface-charge-transfer doping. Appl. Phys. Lett., 2015, 107, (6) 062102.
Willets, et al., Localized surface plasmon resonance spectroscopy and sensing. Annu. Rev. Phys. Chem. 2007, 58, 267-297.
Williams, SE, et al. Controlling the nanoscale patterning of AuNPs on silicon surfaces. Nanomaterials 2013; 3: 192-203.
Xiao, D. et al. Coupled spin and valley physics in monolayers of MoS 2 and other group-VI dichalcogenides. Physical Review Letters 2012, 108(19), 196802.

* cited by examiner e f

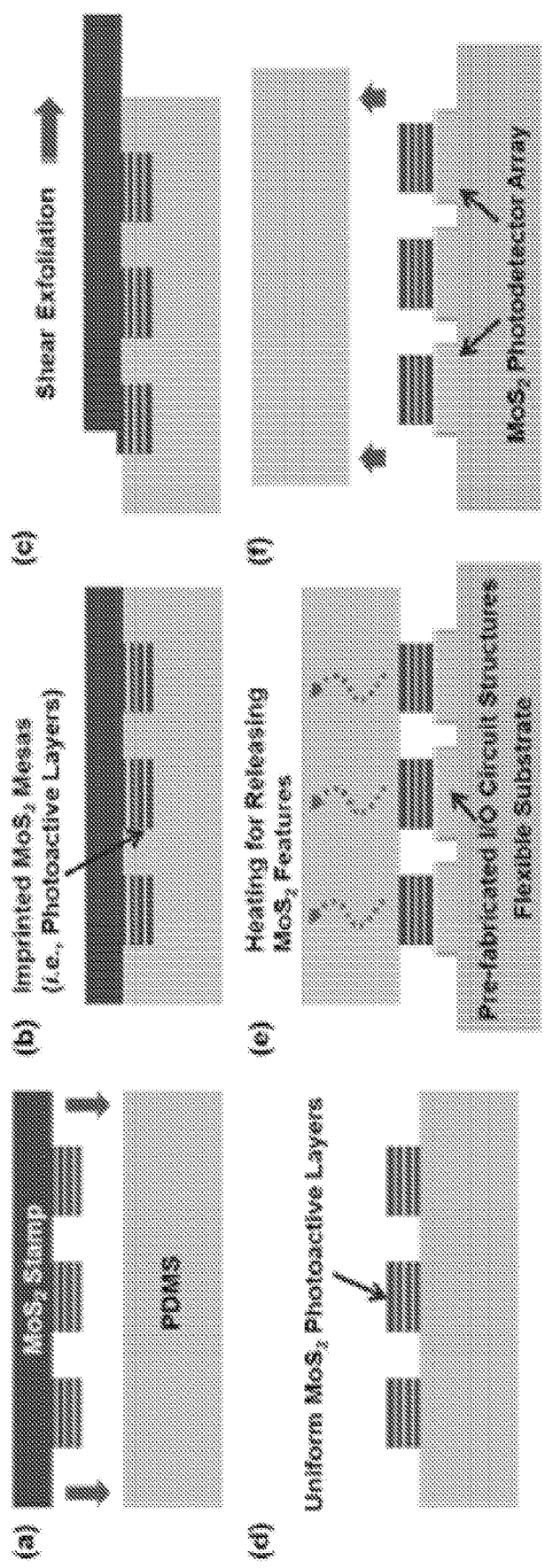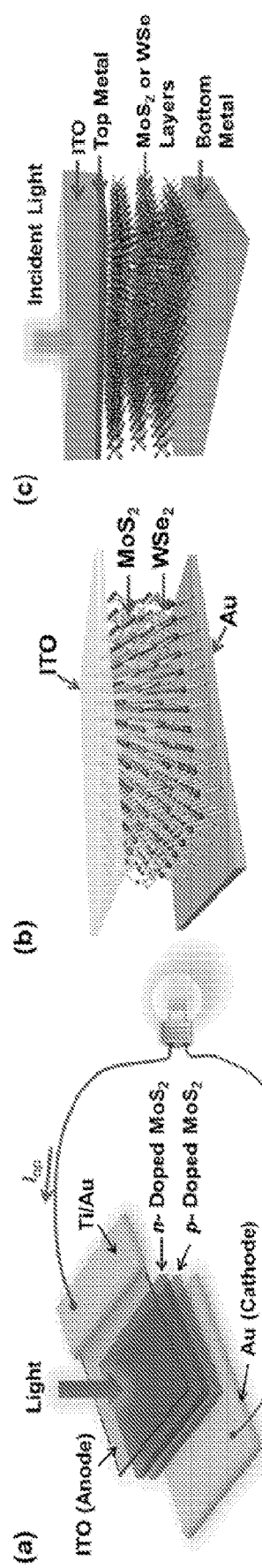
FIG. 10
FIG. 11

PLASMO PHOTOELECTRONIC IMMUNOSENSOR

CROSS-REFERENCE TO RELATED APPLICATIONS

This application is a 371 U.S. National Phase Entry of pending International Application No. PCT/US2018/028856, filed Apr. 23, 2018, which claims the priority benefit of U.S. Provisional Application No. 62/489,872, filed Apr. 25, 2017, which are incorporated herein by reference in their entireties.

STATEMENT REGARDING FEDERALLY SPONSORED RESEARCH OR DEVELOPMENT

This invention was made with government support under grant CBET1263889 awarded by the National Science Foundation. The government has certain rights in the invention.

FIELD OF THE DISCLOSURE

Provided herein are systems and methods for performing assays. In particular, provided herein are systems and methods for performing sensitive and rapid immunoassays.

BACKGROUND

Cytokines are bioactive proteins responsible for cell signaling and regulating the maturation, growth, and responsiveness of immune cells (Opal, S. M. & DePalo, V. A. Chest 117, 1162-1172 (2000); Rothenberg, E. V. Nat. Immunol. 8, 441-444 (2007)). Quantifying cytokines in human serum provides highly valuable clinical information to monitor the immune status of hosts and adjust therapies in different inflammatory disease conditions, such as sepsis (Damas, P., et al. *Crit. Care Med.* 25, 405-412 (1997)), cancer (Lippitz, B. E. Lancet Oncol. 14, E218-E228 (2013)), lupus (Maczynska, I., et al. Immunol. Lett. 102, 79-82 (2006)), and graft-versus-host disease (GVHD) (Visentainer, J. E. L., et al. Exp. Hematol. 31, 1044-1050 (2003)). Given the complexity and dynamic nature of the human immune system, detection and trending of biomarker signatures and subtle changes occurring during a diseased state requires rapid analysis of a complex panel of multiple cytokines at high accuracy, sensitivity and throughput. However, conventional methods based on fluorescence sandwich immunoassays fall short of meeting this demand as they face stringent limitations on their practical implementation in an ideal immune monitoring approach. These limitations arise primarily due to the need for multiple time-consuming labeling and washing processes while consuming a large sample volume. At present, no assay exists that satisfies all the requirements of near-real-time immune status monitoring that involve analysis of complex biological samples.

Systems and methods for sensitive and rapid immunoassays are needed.

SUMMARY

Provided herein are systems and methods for performing assays. In particular, provided herein are systems and methods for performing sensitive and rapid immunoassays.

The devices, systems, and methods described herein provide continuous, label-free, and sensitive detection of a variety of analytes, including multiplex applications. The devices find use in a variety of research, screening, and clinical applications.

For example, in some embodiments, provided herein is a localized surface plasmon resonance device (LSPR), comprising: a nanoplasmonic filter comprising an array of metallic nanoparticles comprising antigen-binding molecules (e.g., antibodies) specific for at least one (e.g., at least 1, 2, 3, 5, 10, or 20) analyte (e.g., polypeptide) on an optically transparent dielectric (e.g., $SiO_2$) layer; and a photoconductive flake comprising a few-layer $MoS_2$ layer (e.g., 10-50 nm (e.g., 5, 10, 14, 15, 16, 20, or 30 nm)). In some embodiments, the nanoplasmonic filter and said photoconductive flake layer are separated by a 10-1000 µm (e.g., 10, 100, 150, 170, 200, 300, 500, 750, or 1000 µm) deep air space. In some embodiments, the particles are gold nanoparticles or gold rods. In some embodiments, the device comprises a substrate (e.g., glass or thermoplastic). In some embodiments, the substrate is flexible. In some embodiments, the device further comprises a plurality of microfluidic channels in communication with said device. In some embodiments, the device comprises an inlet in operable communication with the microfluidic channels. In some embodiments, the inlet comprises an O-ring. In some embodiments, the device further comprises a sample loading channel with micro pillar structures in operable communication with the inlet and the microfluidic channels. In some embodiments, the device is 1-3 cm in width and 3-8 cm in length. In some embodiments, the antibodies comprise a plurality (e.g., 2, 3, 4, 5, 6, 7, 8, 9, 10, or more) of antibodies, wherein each antibody is specific for a different polypeptide. In some embodiments, the polypeptides are cytokines (e.g., chemokines), polypeptides, antibodies, or nucleic acids. In some embodiments, the cytokines are selected from, for example, interleukin-1β (IL-1β), interleukin-2 (IL-2); interleukin-4 (IL-4); interleukin-6 (IL-6); interleukin-10 (IL-10); interferon-gamma (IFN-γ); tumor-necrosis-factor alpha (TNF-α) acylation stimulating protein, adipokine, albinterferon, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL5, CCL6, CCL7, CCL8, CCL9, colony-stimulating factor, CX3CL1, CX3CR1, CXCL1, CXCL10, CXCL11, CXCL13, CXCL14, CXCL15, CXCL16, CXCL17, CXCL2, CXCL3, CXCL5, CXCL6, CXCL7, CXCL9, erythropoietin, Gc-MAF, granulocyte colony-stimulating factor, granulocyte macrophage colony-stimulating factor, hepatocyte growth factor, IL-17, IL1A, IL1B, inflammasome, interferome, interferon, interferon beta 1a, interferon beta 1b, interferon gamma, interferon type I, interferon type II, interferon type III, interferon-stimulated gene, interleukin 1 family, interleukin 1 receptor antagonist, interleukin 12, interleukin 12 subunit beta, interleukin 13, interleukin 16, interleukin 23, interleukin 23 subunit alpha, interleukin 34, interleukin 35, interleukin 7, interleukin 8, interleukin-36, leukemia inhibitory factor, leukocyte-promoting factor, lymphokine, lymphotoxin, lymphotoxin alpha, lymphotoxin beta, macrophage colony-stimulating factor, macrophage inflammatory protein, macrophage-activating factor, monokine, myokine, myonectin, nicotinamide phosphoribosyltransferase, oncostatin M, oprelvekin, platelet factor 4, proinflammatory cytokine, promegapoietin, RANKL, stromal cell-derived factor 1, talimogene laherparepvec, XCL1, XCL2, XCR1 Interleukin-1, Interleukin-1 receptor antagonist, Interleukin-2, Interleukin-2 receptor antagonist, Interleukin-4, Interleukin-6, Interleukin-8, Interleukin-10, Interleukin-12, Interleukin-17, Interluekin-23, Tumor necrosis factor alpha, Interferon gamma, Granzyme B, HSP1AB, MMP-8, MIP-1a, Chemokine (c-c motif) ligand 3 (Macrophage inflammatory protein 1-alpha), Matrix metalloproteinase-8, or Heat shock protein 70 A1B. In some embodiments, the microfluidic channels are orthogonal to the array of metal particles. In some embodiments, the device comprises at least 5 (e.g., 10 or more) parallel microfluidic channels. In some embodiments, the microfluidic channels have a volume of approximately 10 nl to 10 µl (e.g., 50 to 500 nL). In some embodiments, each of the microfluidic channels has an inlet port and an outlet port. In some embodiments, the microfluidic channels are constructed of PDMS or thermoplastic. In some embodiments, the substrate comprises at least 100 (e.g., at least 200, at least 300, at least 400, at least 500, at least 750, or at least 1000) antibodies.

Further embodiments provide an oral device (e.g., mouthguard or mouthpiece) comprising the devices described herein.

Further embodiments provide a system, comprising a) any of the aforementioned devices; and b) a LSPR detection apparatus. In some embodiments, the system further comprises one or more of a sample handling component, a data analysis component, or a user interface.

Additional embodiments provide a method of measuring levels of one or more polypeptides, comprising a) contacting the system described herein with a sample (e.g., a sample from a subject); and b) measuring the level of one or more polypeptides in the sample using LSPR. In some embodiments, the detection is multiplex detection of two or more distinct polypeptides. In some embodiments, the polypeptides are cytokines. In some embodiments, the sample is a biological sample (e.g., including but not limited to, serum, blood, urine, sputum, CSF, or saliva). In some embodiments, the level of the cytokines is indicative of the presence of an inflammatory response (e.g., associated with sepsis, cancer, lupus, or graft-versus-host disease (GVHD)), an immune response, organ damage, or infection in the subject. In some embodiments, the subject is undergoing chemotherapy, cell or gene based therapy, immunomodulation, or surgery. In some embodiments, the results of the measuring are used to determine a treatment course of action in the subject (e.g., administration of an immune suppressant, a drug that blocks the activity of a cytokine (e.g., etanercept and/or tocilizumab), anti-rejection drug (e.g., tacrolimus), or a drug comprising recombinant proteins (e.g., sargramostim and/or filgrastim). In some embodiments, the measuring is completed in 2 hours (e.g., 1 hour, 50 minutes, 45 minutes, 40 minutes, 35 minutes, 30 minutes, 25 minutes, 20 minutes, 15 minutes, 10 minutes, 5 minutes or less). In some embodiments, the contacting comprises inserting said device in the mouth of the subject. In some embodiments, the device is integrated into an oral device (e.g., mouthguard or mouthpiece). In some embodiments, the device remains in the mouth of the subject for at least one hour (e.g., at least 1 hour, 8 hours, 12 hours, 1 day, 2 days, one week, or longer). In some embodiments, the measuring is repeated at least once (e.g., once, twice, five times, 10 times, or continuously).

Additional embodiments are described herein.

DESCRIPTION OF THE FIGURES

FIG. 10 shows integration of MoS$_2$ photodetector arrays on flexible substrates bearing pre-structured I/O circuits.

FIG. 11 shows three types of MoS$_2$-based photodetectors, including (a) plasma-doped pn-junction detectors, (b) MoS$_2$/$_{WSe2}$ heterojunction detectors, and (c) metal-induced surface-charge-transfer (SCT) detectors.

DEFINITIONS

Figure 1:
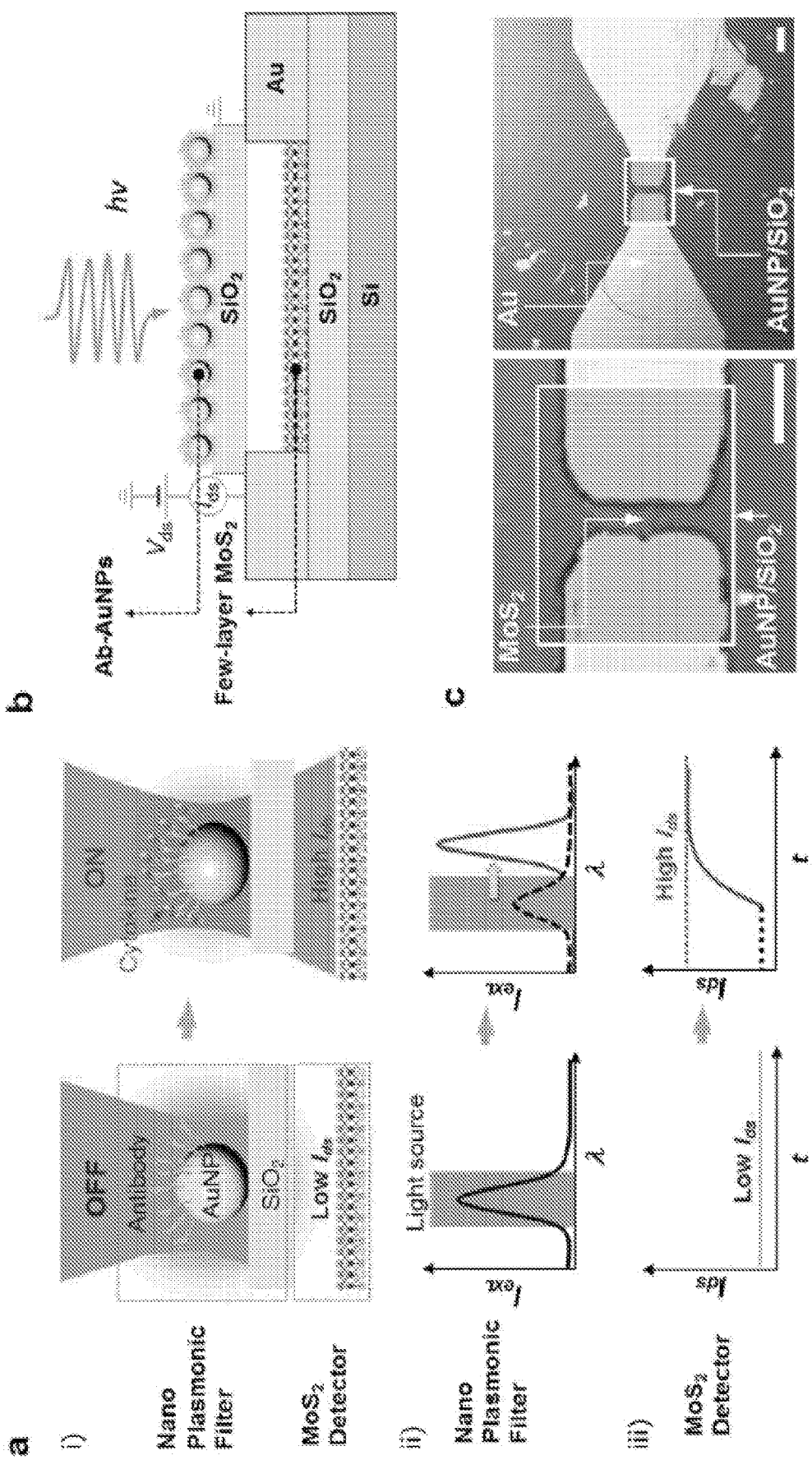
FIG. 1 shows a bio-tunable nanoplasmonic filter on a few-layer $MoS_2$ photodetector. (a) Schematic of decoupled nanoplasmonic filter on few-layer $MoS_2$ sensor for cytokine detection. i) An antibody-attached plasmonic gold nanoparticle (AuNP [d=50 nm]) resonates with incident light at $\lambda$=532 nm. ii) The extinction of the AuNP is matched to the incident light. iii) Resonance between plasmonic extinction of the antibody-AuNP and the incident light source induces a decrease in the amount of the incident light detected in MoS2. (b) Cross-sectional view of the structure of the decoupled nanoplasmonic filter and the few-layer $MoS_2$ photodetector together with electrical connections for device characterization. (c) Optical microscope image of the decoupled $AuNP/SiO_2$ and $MoS_2$ nano flake sensor (scale bar=20 µm).

The term "assay reagents" as used herein is used in the broadest sense and refers to any reagent useful, necessary, or sufficient for performing an assay (e.g., immunoassay). Examples include, but are not limited to, antibodies, controls, buffers, calibration standards and the like.

The term "sample" in the present specification and claims is used in its broadest sense. It is meant to include both biological and environmental samples. A sample may include a specimen of synthetic origin.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present disclosure.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

"Antigen binding molecule" refers to a molecule that binds a specific antigen. Examples include, but are not limited to, proteins, nucleic acids, aptamers, synthetic molecules, etc.

"Antigen binding protein" refers to proteins that bind to a specific antigen. "Antigen binding proteins" include, but are not limited to, immunoglobulins, including polyclonal, monoclonal, chimeric, single chain, and humanized antibodies, Fab fragments, F(ab')2 fragments, and Fab expression libraries.

"Specific binding" or "specifically binding" when used in reference to the interaction of an antibody and an antigen means that the interaction is dependent upon the presence of a particular structure (e.g., the antigenic determinant or epitope) on the antigen; in other words the antibody is recognizing and binding to a specific structure rather than to antigens in general. For example, if an antibody is specific for epitope "A," the presence of a protein containing epitope A (or free, unlabelled A) in a reaction containing labeled "A" and the antibody will reduce the amount of labeled A bound to the antibody.

As used herein, "microfluidic" refers to, for example, a device for transport or storage of small volumes (e.g., of liquids such as assay reagents). In some embodiments, individual channels or chamber of microfluidic devices comprise a volume of 10 nL to 1 μL (e.g., 10, 20, 50, 100, 200, 300, 400, 500, or 750 nL), although other sizes are contemplated.

The terms "test compound" and "candidate compound" refer to any chemical entity, pharmaceutical, drug, and the like that is a candidate for use to treat or prevent a disease, illness, sickness, or disorder of bodily function. Test compounds comprise both known and potential therapeutic compounds. A test compound can be determined to be therapeutic by screening using the screening methods of the present disclosure.

DETAILED DESCRIPTION

Provided herein are systems and methods for performing assays. In particular, provided herein are systems and methods for performing sensitive and rapid immunoassays.

LSPR is a plasmonic phenomenon that arises around nanoscale structures or nanoparticles of noble metal (e.g., ruthenium, cesium, palladium, silver, gold, iridium, platinum, gold, and combinations thereof) when light is illuminated onto a nanoscale featured sensing surface. When the incident light frequency matches the natural frequency of electron oscillation of the conductive metal nanoparticles, the interactions between the incident light and the nanostructured surface maximize the optical extinction of the particles with electrons highly enhanced near the particles' surfaces and trigger the LSPR. The resonance wavelength and intensity can be readily modified by the temporal or irreversible absorption of analyte as small as protein, nucleic acids and cytokines. As such, it has been proven to be an effective label-free detection method for antibody-antigen binding that permits high-sensitivity and real-time analysis. In addition, the elimination of secondary antibody labeling can significantly suppress cross-reactivity. Since the sensor elements used in LSPR technique can be as small as a few tens of nanometers in diameter, it provides a significant advantage in constructing a large number of sensor arrays integrated on a single chip, which enables a high-throughput, high multiplicity sensing platform with drastically reduced sample volume and total assay time.

Monitoring of the time-varying immune status of a diseased host often requires rapid and sensitive detection of cytokines. Metallic nanoparticle-based localized surface plasmon resonance (LSPR) biosensors hold promise to meet this clinical need by permitting label-free detection of target biomolecules. These biosensors, however, continue to suffer from relatively low sensitivity as compared to conventional immunoassay methods that involve labelling processes. Their response speeds also need to be further improved to enable rapid cytokine quantification for critical care in a timely manner. Described herein is a biosensor integrating a nanoplasmonic filter and a highly sensitive few-layer molybdenum disulfide ($MoS_2$) photoconductive component, which serves as a generic device platform to meet the need of rapid cytokine detection with high sensitivity. In some embodiments, the nanoplasmonic filter includes anti-cytokine antibody-conjugated gold nanoparticles (AuNPs) on a $SiO_2$ thin layer that is placed, for example, 170 μm above a few-layer $MoS_2$ photoconductive flake device. The principle of the biosensor operation is based on tuning the delivery of incident light to the few-layer $MoS_2$ photoconductive flake thorough the nanoplasmonic filter. The tuning is dependent on cytokine concentration in the nanoplasmonic filter. Using the developed LSPR-modulated optoelectronic biosensor, label-free detection of IL-1β, a pro-inflammatory cytokine, with detection limit as low as 250 fg/mL (14 fM) and a short assay time of 10 min was demonstrated.

Owing to their attractive electronic/optical properties, large abundance, and compatibility to planar nanofabrication processes, atomically layered semiconducting materials, such as $MoS_2$, $WSe_2$, and $WS_2$, have recently garnered much attention as promising candidates for development of high-performance field-effect transistors (FETs) and other relevant nanoelectronic devices. The transport characteristics of monolayer or few-layer $MoS_2$ FET channels are extremely sensitive to the external stimuli and can be exploited to make biosensors with high sensitivity and fast response speed. 25-26 Electrical response characteristics of such $MoS_2$ FET devices have been used to create ultrasensitive biosensors capable of detecting antigen-antibody binding events 0.27-28 However, such purely electrical and electronic biosensors still suffer from degradation of detection stability and sensitivity over a long incubation time, which is attributed to ionic screening of electric field and unwanted short-circuit effects in an aqueous environment. 29-32 Specifically, the ions in an aqueous solution and other heterogeneous liquid components could result in serious shorting of electric circuits and distract electron current distribution in the presence of direct contact between the biomolecules and transistor regions. In this regard, alternative sensing mechanisms such as those in the sensors described herein are needed to prevent the $MoS_2$-based sensing component from directly contacting with liquid reagents.

The devices find use, for example, in research, screening, point-of-care diagnosis, wearable bio/chemical sensing, and environmental monitoring. Exemplary devices, systems, and methods are described herein.

I. Devices and Systems

Embodiments of the present disclosure provide devices and systems for use in LSPR immunoassays. In some embodiments, devices comprise a LSPR component and a microfluidic component. The present disclosure further provides systems for performing LSPR using the described devices.

A. LSPR surfaces

For example, in some embodiments, provided herein is a localized surface plasmon resonance device (LSPR), comprising: a nanoplasmonic filter comprising an array of metallic nanoparticles comprising antibodies specific for at least one (e.g., at least 1, 2, 3, 5, 10, or 20) analytes (e.g., polypeptides, nucleic acids, cells, cell fragments, etc.) on an optically transparent dielectric (e.g., $SiO_2$) layer; and a photoconductive flake comprising a few-layer $MoS_2$ layer (e.g., 10-50 nm (e.g., 5, 10, 14, 15, 16, 20, or 30 nm) (See e.g., U.S. 20170102357; herein incorporated by reference in its entirety)). In some embodiments, the nanoplasmonic filter and said photoconductive flake layer are separated by a 10-1000 μm (e.g., 10, 100, 150, 170, 200, 300, 500, 750, or 1000 μm) deep air space. In some embodiments, the particles are gold nanoparticles or gold rods. Examples 1 and 2 below describe construction, properties, and analysis of LSPR devices of embodiments of the present disclosure.

In some embodiments, devices comprise a substrate (e.g. solid surface). In some embodiments, the solid surface is glass. In some embodiments, the solid surface is a flexible plastic or other material. Surfaces include, but are not limited to, transparent plastics, such as poly(methyl methacrylate) (PMMA), known as acrylic glass, a transparent thermoplastic that can be modified with surface moieties for antibody function; polycarbonate; cyclic olefin copolymer (COC); cyclo olefin polymer (COP); polystyrene; polypropylene; and polyethylene terephthalate glycol-modified (PEGT).

In some embodiments, substrates are coated with metals that allow for the resonant oscillation of conduction electrons at the interface between a negative and positive permittivity material stimulated by incident light. This can occur as deposition of bulk material allowing detection of surface plasmon resonance (SPR), or as described herein as discrete plasmonic nanoparticles allowing detection of localized plasmon resonance (LSPR). Metals that support surface plasmons include, but are not limited to, silver, gold, copper, titanium or chromium. In some embodiments metals are provided as localized nanotubes or other geometric configurations. In some exemplary embodiments, metal nanorods or other metal configurations are arranged in stripes or other regular patterns on the surface (See e.g., Williams S E, Davies P R, Bowen J L, and Allender C J. Controlling the nanoscale patterning of AuNPs on silicon surfaces. Nanomaterials 2013; 3: 192-203; herein incorporated by reference in its entirety). In addition to nanorods, other suitable particle configurations include, but are not limited to, nanospheres, nanostars, nanodiamonds, nanopyramids, nanobipyramids, or nanorings and metal core-shell structures (e.g., gold/silver core-shell structures). Silver exhibits good optical properties but may be toxic in a biological environment due to the release of silver ions. The chemically inert gold nanoshell provides biocompatibility while maintaining the extraordinary optical properties of the silver core. In some embodiments, other noble metals are utilized (e.g., ruthenium, rhodium, palladium, osmium, iridium, platinum).

In some embodiments, metallic surfaces or areas are functionalized with antibodies (e.g., monoclonal or polyclonal antibodies) or other analyte specific binding partners (e.g., aptamers, antibody fragments, etc.) that bind to a specific peptide or polypeptide (e.g., antigen). The present disclosure is not limited to particular antibodies. In some embodiments, antibodies are specific for a cytokine or chemokine (e.g., one or more of interleukin-2 (IL-2); interleukin-4 (IL-4); interleukin-6 (IL-6); interleukin-10 (IL-10); interleukin-(IL-8); interleukin-12 (IL-12) interferon-gamma (IFN-γ); or tumor-necrosis-factor alpha (TNF-α)). Additional cytokines include, but are not limited to, acylation stimulating protein, adipokine, albinterferon, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL5, CCL6, CCL7, CCL8, CCL9, colony-stimulating factor, CX3CL1, CX3CR1, CXCL1, CXCL10, CXCL11, CXCL13, CXCL14, CXCL15, CXCL16, CXCL17, CXCL2, CXCL3, CXCL5, CXCL6, CXCL7, CXCL9, erythropoietin, Gc-MAF, granulocyte colony-stimulating factor, granulocyte macrophage colony-stimulating factor, hepatocyte growth factor, IL-17, IL1A, IL1B, inflammasome, interferome, interferon, interferon beta 1a, interferon beta 1b, interferon gamma, interferon type I, interferon type II, interferon type III, interferon-stimulated gene, interleukin 1 family, interleukin 1 receptor antagonist, interleukin 12, interleukin 12 subunit beta, interleukin 13, interleukin 16, interleukin 23, interleukin 23 subunit alpha, interleukin 34, interleukin 35, interleukin 7, interleukin 8, interleukin-36, leukemia inhibitory factor, leukocyte-promoting factor, lymphokine, lymphotoxin, lymphotoxin alpha, lymphotoxin beta, macrophage colony-stimulating factor, macrophage inflammatory protein, macrophage-activating factor, monokine, myokine, myonectin, nicotinamide phosphoribosyltransferase, oncostatin M, oprelvekin, platelet factor 4, proinflammatory cytokine, promegapoietin, RANKL, stromal cell-derived factor 1, talimogene laherparepvec, XCL1, XCL2, and XCR1.

Additional suitable analytes include, but are not limited to, Interleukin-1, Interleukin-1 receptor anatagonist, Interleukin-2, Interleukin-2 receptor antagonist, Interleukin-4, Interleukin-6, Interleukin-8, Interleukin-10, Interleukin-12, Interleukin-17, Interluekin-23, Tumor necrosis factor alpha, Interferon gamma, Granzyme B, HSP1AB, MMP-8, MIP-1a, antibodies (e.g., monoclonal or polyclonal), nucleic acids (e.g., DNA, mRNA, miRNA, lncRNA), nucleic acid probes, Chemokine (c-c motif) ligand 3 (Macrophage inflammatory protein 1-alpha), Matrix metalloproteinase-8, and Heat shock protein 70 A1B.

In some embodiments, linkers are utilized to attach antibodies to surfaces (e.g., using carbodiimide (e.g., EDC (1-Ethyl-3-(3-dimethylaminopropyl)-carbodiimide))/NHS chemistry). In some embodiments, linker is a bifunctional thiol linker. The present disclosure is not limited to the length of the linker. In some embodiments, the linker comprises a 1 to 10 carbon atom chain (e.g., 1, 2, 3, 4, 5, 6, 7, 8, 9, or 10 carbons).

Surfaces (e.g., glass or thermoplastic surfaces) are generated using any suitable method. In some embodiments, the method described in Examples 1 and 2 is utilized.

Other suitable protocols for functionalizing surfaces include, but are not limited to, APTES functioned glass or thermoplastic covalently interact with gold nanorods (Kathryn Mayer et. al., *ACS Nano*, 2, 687-692, 2008; herein incorporated by reference in its entirety); Silane functioned surfaces covalently interact with citrate stabilized god nanoparticles (Maniraj Bhagawati et. al. *Anal. Chem.*, 85, 9564-9571, 2013; herein incorporated by reference in its entirety); and random deposited CTAB gold nanorods with aptamers for detection (Christina Rosman et. al. Nano Lett. 13, 3243-3247, 2013; herein incorporated by reference in its entirety).

In some embodiments, surfaces are silanized (See e.g., Haddada M B, et al. Gold Bull 2013; 46: 335-341; Cant N E, et al. Thin Solid Films 2003; 426: 31-39). In some embodiments, silanes are aminated, thiolated, or disulfide modified. In some embodiments, silanization is performed via chemical vapor deposition (e.g., plasma-enhanced CVD or low pressure CVD or via protic solvent).

B. Microfluidic Component

In some embodiments, devices of embodiments of the present disclosure comprise a microfluidic component. The microfluidic component is in fluid communication with the LSPR component and serves to transport assay components (e.g., patient samples and assay reagents) to the LSPR component. In some embodiments, the microfluidic component comprises a plurality (e.g., 2, 4, 6, 8, 10, 12 or more depending on the size of the device) of microfluidic channels. In some embodiments, channels have outlet and inlet components and/or reservoir components for supplying fluids to regions the device. In some embodiments, microfluidic channels are placed perpendicular to LSPR patterned components.

In some embodiments, the device comprises an inlet in operable communication with the microfluidic channels. In some embodiments, the inlet comprises an O-ring to isolate sample in the sample loading channel. In some embodiments, the device further comprises a sample loading channel with micro pillar structures in operable communication with the inlet and the microfluidic channels. The micro pillar structures serve to filter solid contaminants present in saliva. In some embodiments, the device is 1-3 cm in width and 3-8 cm in length.

The microfluidic component is constructed of any suitable material. In some embodiments, layers are made by supplying a negative "master" and casting a castable material over the master. Castable materials include, but are not limited to, polymers, including epoxy resins, curable polyurethane elastomers, polymer solutions (e.g., solutions of acrylate polymers in methylene chloride or other solvents), curable polyorganosiloxanes, and polyorganosiloxanes which predominately bear methyl groups (e.g., polydimethylsiloxanes ("PDMS")). Curable PDMS polymers are available from many sources. Both addition curable and condensation-curable systems are available, as also are peroxide-cured systems. All these PDMS polymers have a small proportion of reactive groups which react to form crosslinks and/or cause chain extension during cure. Both one part (RTV-1) and two part (RTV-2) systems are available.

In some embodiments, transparent devices are desirable. Such devices may be made of glass or transparent polymers.

PDMS polymers are well suited for transparent devices. A benefit of employing a polymer that is slightly elastomeric is the case of removal from the mold and the potential for providing undercut channels, which is generally not possible with hard, rigid materials. Methods of fabrication of microfluidic devices by casting of silicone polymers are well known. See, e.g. D. C. Duffy et al., "Rapid Prototyping of Microfluidic Systems in Poly(dimethylsiloxane)," Analytical Chemistry 70, 4974-4984 (1998). See also, J. R. Anderson et al., Analytical Chemistry 72, 3158-64 (2000); and M. A. Unger et al., Science 288, 113-16 (2000), each of which is herein incorporated by reference in its entirety.

In some embodiments, fluids are supplied to the device by any suitable method. Fluids may, for example, be supplied from syringes, from microtubing attached to or bonded to the inlet channels, etc.

Fluid flow may be established by any suitable method. For example, external micropumps suitable for pumping small quantities of liquids are available. Micropumps may also be provided in the device itself, driven by thermal gradients, magnetic and/or electric fields, applied pressure, etc. Integration of passively-driven pumping systems and microfluidic channels is described by B. H. Weigl et al., Proceedings of MicroTAS 2000, Enshede, Netherlands, pp. 299-302 (2000).

In some embodiments, fluid flow is established by a gravity flow pump, by capillary action, or by combinations of these methods. A simple gravity flow pump comprises a fluid reservoir either external or internal to the device, which contains fluid at a higher level (with respect to gravity) than the respective device outlet. Such gravity pumps have the deficiency that the hydrostatic head, and hence the flow rate, varies as the height of liquid in the reservoir drops. For many devices, a relatively constant and non-pulsing flow is desired.

To obtain constant flow, a gravity-driven pump as disclosed in published PCT application No. WO 03/008102 A1 (Jan. 18, 2002), herein incorporated by reference, may be used. In such devices, a horizontal reservoir is used in which the fluid moves horizontally, being prevented from collapsing vertically in the reservoir by surface tension and capillary forces between the liquid and reservoir walls. Since the height of liquid remains constant, there is no variation in the hydrostatic head.

Flow may also be induced by capillary action. In such a case, fluid in the respective channel or reservoir will exhibit greater capillary forces with respect to its channel or reservoir walls as compared to the capillary forces in the associated device. This difference in capillary force may be brought about by several methods. For example, the walls of the outlet and inlet channels or reservoirs may have differing hydrophobicity or hydrophilicity. Alternatively, the cross-sectional area of the outlet channel or reservoir is made smaller, thus exhibiting greater capillary force.

In some embodiments, construction of fluidic devices is by soft lithography techniques as described for example by Duffy et al (Analytical Chem 70 4974-4984 1998; See also Anderson et al, Analytical Chem 72 158-64 2000 and Unger et al., Science 288 113-16 2000). Addition-curable RTV-2 silicone elastomers such as SYLGARD 184, Dow Corning Co can be used for this purpose. The dimensions of the channels are readily determined by volume and flow rate properties etc.

The substrate may be of one layer or plurality of layers. The individual layers may be prepared by numerous techniques including laser ablation, plasma etching, wet chemical methods, injection molding, press molding, etc. Casting from curable silicone is most preferred, particularly when optical properties are important. Generation of the negative mold can be made by numerous methods all of which are well known to those skilled in the art. The silicone is then poured onto the mold degassed if necessary or desired and allowed to cure. Adherence of multiple layers to each other may be accomplished by conventional techniques.

A method of manufacture of some devices employs preparing a master through use of negative photoresist SU-8 50 photoresist from Micro Chem Corp Newton Mass.

In some embodiments, devices are injection molded. For example, in some embodiments, devices comprise injection molded thermoplastic fluidic layers bonded to the detection substrate.

C. Systems

In some embodiments, LSPR signals are detected by any suitable detector. In some embodiments, devices are placed on a movable platform or stage for scanning multiple locations on the device. In some embodiments, detectors comprise a light source, one or more objectives, filters, dark field condensers, and imaging components (e.g., CCD detectors).

In some embodiments, devices are configured for multiplex detection of multiple analytes. For example, as described above, a bar code component is provided by providing specific distinct antibodies in addressable locations on the LSPR surface.

In some embodiments, following imaging, a software component is utilized to analyze signal from the array. For example, in some embodiments, software is configured to process an image, determine which locations have target antigen bound, and provide a report. In some embodiments, binding data is quantitative. For example, in some embodiments, a calibration curve is obtained prior to performing the assay and/or in parallel on each chip (e.g., as internal positive and negative controls).

In some embodiments, a computer-based analysis program is used to translate the raw data generated by the detection assay (e.g., the presence, absence, or level of an antigen) into data of predictive value for a clinician (e.g., choice of therapy). The clinician can access the predictive data using any suitable means. Thus, in some preferred embodiments, the present disclosure provides the further benefit that the clinician, who is not likely to be trained in immunology or molecular biology, need not understand the raw data. The data is presented directly to the clinician in its most useful form. The clinician is then able to immediately utilize the information in order to optimize the care of the subject.

The present disclosure contemplates any method capable of receiving, processing, and transmitting the information to and from laboratories conducting the assays, information provides, medical personal, and subjects. For example, in some embodiments of the present disclosure, a sample (e.g., a saliva, blood, urine or serum sample) is obtained from a subject and submitted to a profiling service (e.g., clinical lab at a medical facility, profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (e.g., levels of antigens), specific for the diagnostic or prognostic information desired for the subject.

The profile data is then prepared in a format suitable for interpretation by a treating clinician. For example, rather than providing raw data, the prepared format may represent a diagnosis or risk assessment (e.g., likelihood of organ rejection or immune response) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

In some embodiments, systems comprising devices, detectors, software, and computer components (e.g., computer processor and display screen, smart phone, etc.) are provided. In some embodiments, the detection and analysis components are provided as a platform and the devices are provided as cartridges or plates (e.g., disposable or re-usable devices). For example, in some embodiments, the portion of the system that contacts patient sample is provided as a disposable cartridge or strip and the detection and analysis platform is a standalone reusable component that can accept and analyze cartridges specific for one or more target antigens.

In some embodiments, the device is provided as a wearable oral device (e.g., mouth guard or mouth piece) device. In some embodiments, devices are integrated into the mouth guard or other mouth device. In some embodiments, the subject wears the mouth guard for the duration of the monitoring period (e.g., hours, days, weeks, or months). In some embodiments, the mouth guard is inserted into a subject's mouth for monitoring and removed after monitoring. In some embodiments, the mouth guard allows for continuous monitoring in a hospital or home setting.

In some embodiments, the system comprises a hand held device (e.g., suitable for bedside use). In some embodiments, handheld devices comprise a disposable strip or cartridge for patient sample. In some embodiments, handheld devices are target specific (e.g., dedicated to a specific antigen) or target independent (e.g., suitable for accepting different cartridges or strips specific for different antigens).

II. Methods

Embodiments of the present disclosure provide the use of the devices and systems described herein for detection of antigens (e.g., in patient samples). In some embodiments, the entire assay is completed in one hour (e.g., 50 minutes, 40, minutes, 30 minutes, 20 minutes, 10 minutes, 5 minutes, 4 minutes, 3 minutes, 2 minutes, 1 minute, etc.) or less. This provides a distinct advantage over traditional ELISA assays, which often require multiple hours to complete. Such rapid assays are especially useful in patient care settings where decisions about treatment and interventions need to be made rapidly.

The present disclosure is not limited to particular patient samples. Examples include, but are not limited to, serum, whole blood, urine, sputum, semen, cerebral spinal fluid (CSF), or saliva. In some embodiments, samples are processed or purified prior to use. In some embodiments, samples are utilized without processing (e.g., from a finger prick or urine sample). In some embodiments, sample volumes are 1 µL or less (e.g., 900 nL, 800 nL, 700 nL, 600 nL, 500 nL, 400 nL, 300 nL, 200 nL, or 100 nL or less).

In some embodiments, the present disclosure provides methods for detecting one or more cytokines (e.g., those disclosed herein), chemokines, or other makers of inflammation, immune response, organ damage, or infection. In some embodiments, the presence and/or levels of the cytokines in the sample is used to determine the presence of an inflammatory response, an immune response, organ damage, or infection in the subject. The present disclosure is not limited to particular inflammatory or immune responses. Examples include, but are not limited to, surgical trauma, sepsis, cancer, lupus, graft versus host disease (GVHD), autoimmune hepatitis, multiple sclerosis, systemic lupus erythematosus, myasthenia gravis, Type I diabetes, rheumatoid arthritis, psoriasis, Hashimoto's thyroiditis, Grave's disease, ankylosing spondylitis, Sjogrens disease, CREST syndrome, scleroderma, Crohn's disease, acute respiratory distress syndrome (ARDS), patients who have under gone solid organ transplants and are receiving immunosuppression therapy, ulcerative Colitis, polyarteritis nodosa, Whipple's disease, primary sclerosing cholangitis, etc.

In some embodiments, the subject is undergoing chemotherapy or has undergone surgery. In some embodiments, the levels of the cytokines are used to determine a treatment course of action. For example, in a patient found to be undergoing GVHD, sepsis, or an inflammatory response, an immune suppressant drug (e.g., steroid) or immune modulating drug (e.g., filgrastim) is administered.

In some embodiments, patients undergoing chemotherapy (e.g., chimeric antigen receptor T-cell therapy (CAR T-cell)), which results in release of cytokines, are monitored to measure cytokine levels. The levels of the cytokines are monitored to determine when patients have cytokine levels that are clinically too high (e.g., result in shock and/or hemodynamic instability). Such patients are administered anti-cytokine therapy (e.g., etanercept and/or tocilizumab). In some embodiments, cytokine levels are monitored to determine when levels have decreased sufficiently to reduce or halt therapy. In some embodiments, patients that do not have elevated levels of cytokines are not administered anti-cytokine therapy.

In some embodiments, patients are monitored (e.g., using bedside devices) multiple times during the course of treatment, recovery from surgery, or after treatment with an immune suppressing drug to determine if changes in treatment are needed. For example, in some embodiments, patient found to need immune suppressing therapy are monitored to determine when the inflammation or GVHD has subsided in order to determine that a decrease in dosage or discontinuation of treatment is advisable.

EXPERIMENTAL

Example 1

Methods

Chemicals: Gold nanoparticle (gold nanosphere (AuNPs, d=50 nm) and gold nanorod (AuNRs, d1/d2=40/68 nm) were purchased from NanoSeedz™. 3-Aminopropyl triethoxysilane (APTES) 10-Carboxy-1-decanethiol (C-10) and Albumin, from bovine serum (BSA), were purchased from Sigma Aldrich. 1-ethyl-3-[3-dimethylaminopropyl] carbodiimide (EDC) and/Nhydroxysuccinimide (NHS) were purchased from Thermo Co. Ltd. IL-1β and Anti IL-1β were purchased from Life Technologies, Frederick, Md. polydimethylsiloxane (PDMS) elastomer and curing agent were purchased from Coring. Nano pure deionized (DI) water (18.1 MΩ-cm) was produced in-house.

Nano Plasmonic Filter: 1) Plasmonic structure: To prepare the gold nanostructure, gold nanospherical particle (AuNP) and gold nanorod (AuNR) stock solutions (0.2 nM) were centrifuged three times at 5000 rpm for 10 min, and washed them in D.I. water to remove excessive structure direction agents (citrate for AuNP and cetrimonium bromide (CTAB) for AuNR) in the solutions. As a substrate, a thin $SiO_2$ layer (100 um) was used. The $SiO_2$ substrate was rinsed with acetone, isopropanol and DI water. Piranha clean with a solution of $H_2SO_4:H_2O_2=3:1$ v/v was followed for 30 min. The $SiO_2$ substrate was washed with D.I. water carefully. After drying, the surface of the $SiO_2$ substrate was treated by $O_2$ plasma for 2 min at 18 W (COVANCE 1-MP, Femto). Then, hydroxyl groups on the $SiO_2$ substrate are created on the surface. Then the $SiO_2$ substrate was incubated in a 0.1M (3-Aminopropyl) triethoxysilane (APTES) solution for 6 hrs. The AuNP (or AuNR) solution was then loaded into a chamber and incubated overnight. The inlets and outlets were sealed with a cover glass to prevent evaporation and avoid dry-out of the AuNP (or AuNR) solution during incubation. After the incubation, the AuNPs-$SiO_2$ (or AuNR—$SiO_2$) substrate was washed with DI water and strong air blowing was followed.

2) Antibody-gold nanoparticle: After preparation of the AuNP (or AuNR) array on the $SiO_2$ substrate, functionalization of thiolated alkane 10-Carboxy-1-decanethiol (HS—(CH2)10-COOH) using a self-assembly method (SAM) was followed. At first, the $SiO_2$ substrate was incubated in 1 mM of thiolated alkane 10-Carboxy-1-decanethiol (HS—(CH2)10-COOH) overnight. Then the formed carboxylic group (—COOH) on the AuNP surface was used to attach a linker for antibody. The antibody linking was performed by way of the antibody binding to the —COOH functional group through standard 1-ethyl-3-[3-dimethylaminopropyl]carbodiimide/N-hydroxysuccinimide (EDC/NHS) coupling chemistry. After washing the —COOH formed AuNP (or AuNR)—SiO2 substrate, a mixture of 0.4 M EDC and 0.1 M NHS was loaded at a 1:1 volume ratio in a 0.1 M EDC solution into the chamber to activate the AuNP (or AuNR) array surfaces on the $SiO_2$ substrate. Then, to attach the antibody, diluted primary cytokine antibodies from 100 to 10 μg/mL in 1×PBS were prepared and loaded into the chamber and incubated at room temperature for 60 min. To suppress the non-specific binding on the detection surface, the prepared Anti-AuNP (or Anti-AuNR) conjugates were treated with 10 pL of 1% BSA in 1×PBS in blocking buffer and incubated the whole system for 20 min. Before detecting cytokines, the Anti-AuNP (or Anti-AuNR) array surface was thoroughly washed to remove any excessive solutions or molecules using 204, of 1×PBS.

Figure 7:
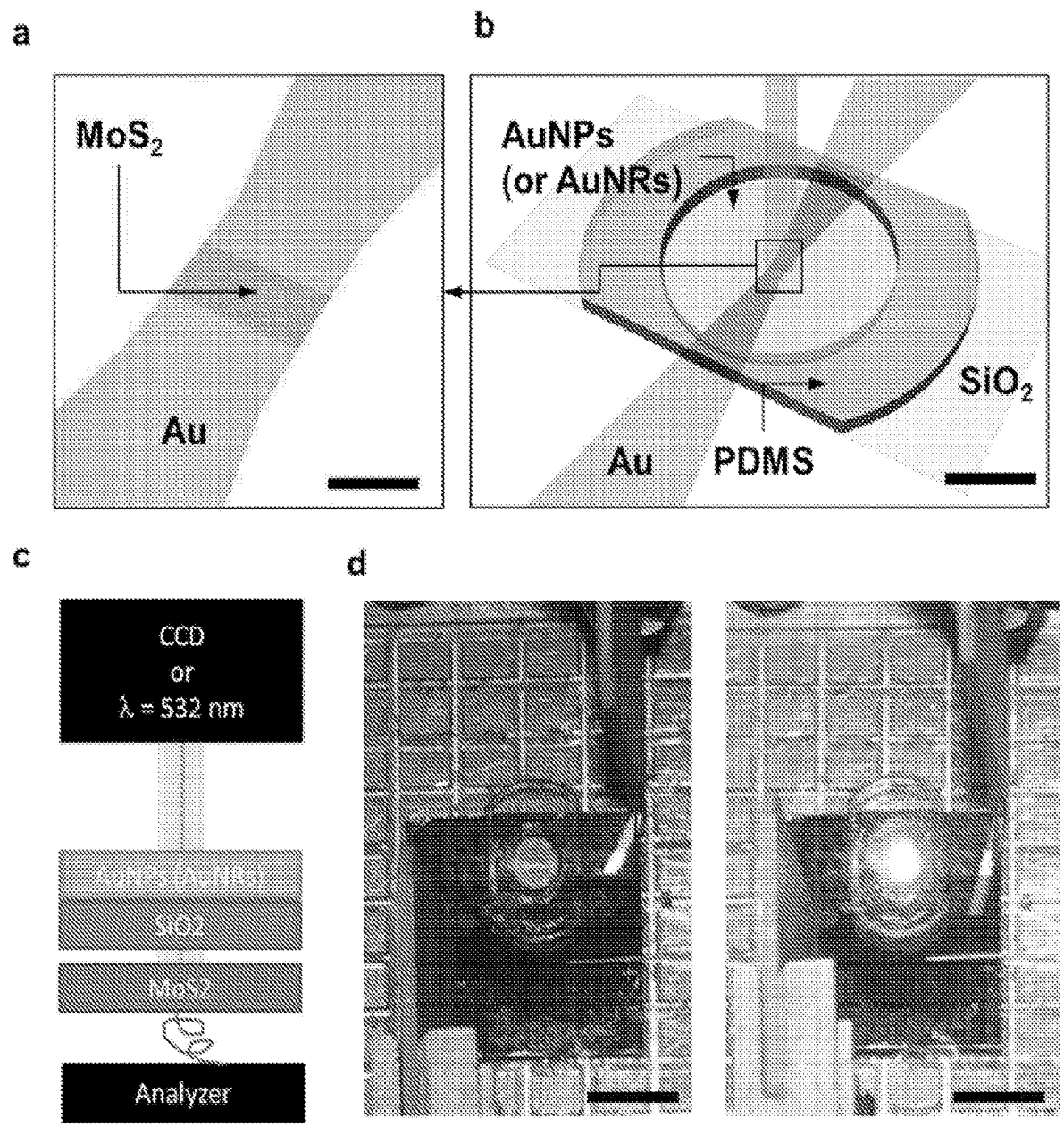
FIG. 7 shows schematics of device design and optical setup of integrated nanoplasmonic optical filter and atomically layered MoS$_2$ photodetector for highly sensitive and rapid cytokine detection with LSPR biosensor microarray. a) Atomically layered MoS$_2$ photodetector between two Au electrodes (Scale bar=20 μm), b) Nanoplasmonic optical filter device (PDMS chamber, plasmonic probe, and SiO$_2$ substrate) design (Scale bar=1 mm), c) Schematic of optical setup, and d) Photo images of device, electrodes and detection bay with laser on (left) and off (right) (Scale bar=7 mm).

Highly sensitive few-layer $MoS_2$ photodetector:

1) Fabrication and Characterization of $MoS_2$ transistor biosensors (FIG. 7): The fewlayer $MoS_2$ thin-film transistors were fabricated using a micro printing method (Nam et al., ACS nano 2013, 7 (7), 5870-5881). Flake $MoS_2$ channel thicknesses were specifically controlled to be 15-20 nm. Such a $MoS_2$ thickness range has been demonstrated to result in the optimal field-effect mobility values for $MoS_2$ transistors. The transistor channel lengths (L) were ~10 μm and the channel widths (W) ranged from 5 μm. Ti (5 nm)/Au (50 nm) electrode pairs served as drain (D) and source (S) contacts, which were created using photolithography followed by metal deposition and lift-off The p+-Si substrates were used as the back gates (G). Thermally grown $SiO_2$ layers (300 nm thick) were used as the back-gate dielectrics. Such thin $SiO_2$ layers can enable a simple color coding method whereby $MoS_2$ flakes with suitable thicknesses (e.g., 15-20 nm) may be quickly identified.

2) Integration of Nanoplasmonic filter and a few-layer $MoS_2$ photodetector device: After separately preparing a AuNP/$SiO_2$ nanoplasmonic optical filter thin layer and an atomically layered $MoS_2$ photodetector, they were assembled into the same device platform. Using macro manipulation control, the AuNP/$SiO_2$ was placed on Au electrode of $MoS_2$ detection platform. Along the alignment marks in both $SiO_2$ substrates of Au/$SiO_2$ and $MoS_2$/$SiO_2$, constant location between nanoplasmonic filter and $MoS_2$ photodetector was made. To avoid any alignment change, the nanoplasmonic optical filter and $MoS_2$ photodetector were physically bonded using a dielectric sticky PDMS thin (0.5 mm) handling layer.

Figure 8:
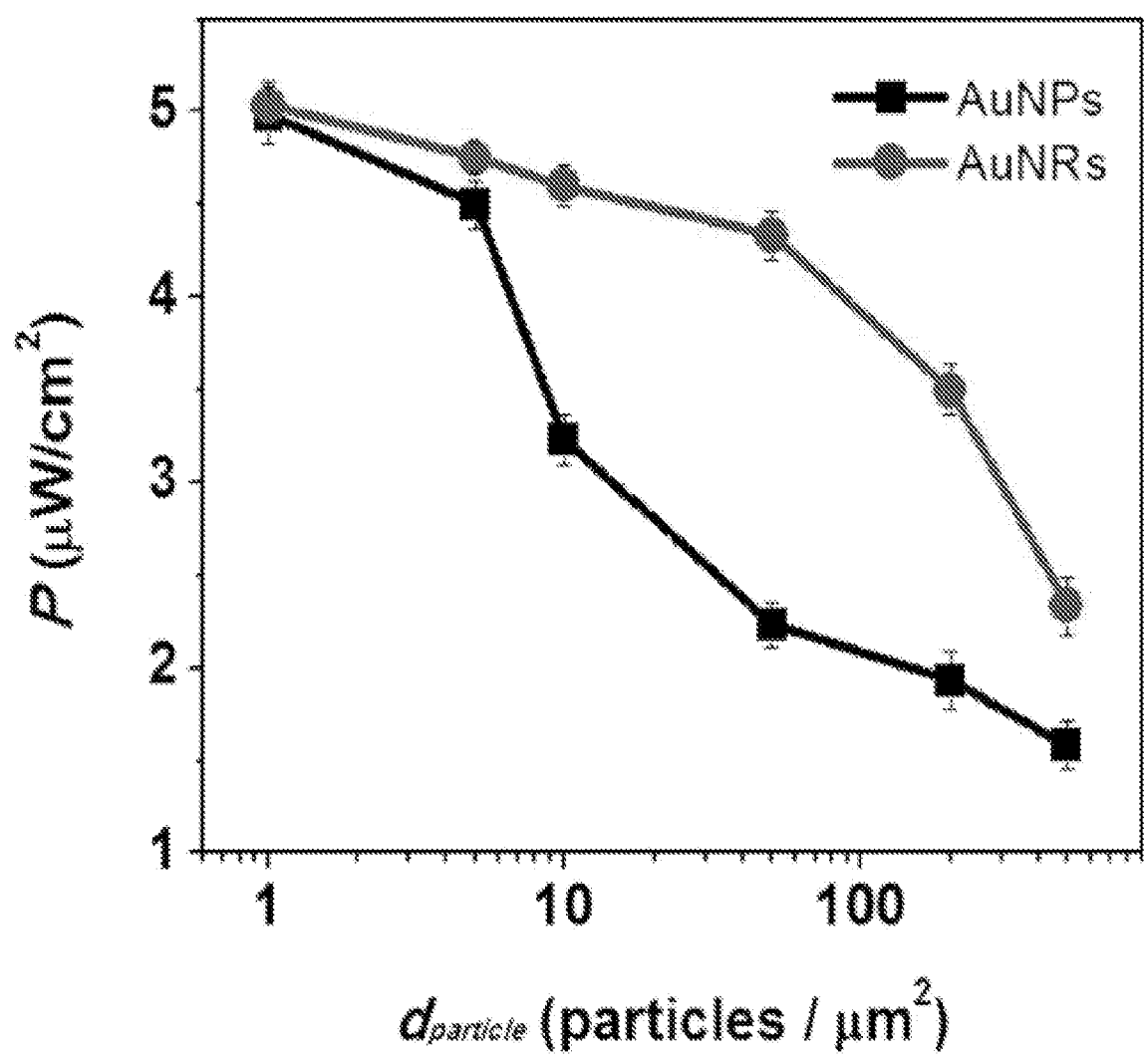
FIG. 8 shows power density measurement with varying particle density on SiO$_2$ substrate.

3) Photo current measurement: All electrical measurements were performed using an HP-4145B semiconductor parameter analyzer. A 532 nm laser (power density, 5 mW/cm$^2$) was also employed to characterize the PV response performance of the devices under light illumination. Even though sensitivity is lower than it of $MoS_2$ photodetector, as a reference, power density through the plasmonic nano filter was also confirmed by conventional power meter (Newport, 843-R) (FIG. 8).

4) LSPR peak shift measurement Protocol: The fabricated and prepared LSPR biosensor microarray chip was mounted on a motorized stage (ProScan, Prior Scientific) to position the on chip sensing spot at ease and to automate the signal scanning. A dark-field condenser (NA=1.45, MBL12000, Nikon) was closely placed to the backside of the glass substrate (the opposite side of the AuNPs (or AuNRs)-deposited sensor side) using lens oil. The light scattered from the AuNR nanoplasmonic biosensor arrays was collected using a 20× objective lens under the chip. The spectrum was collected by a spectrometer (Ocean optics, USB 4000).

Figure 2:
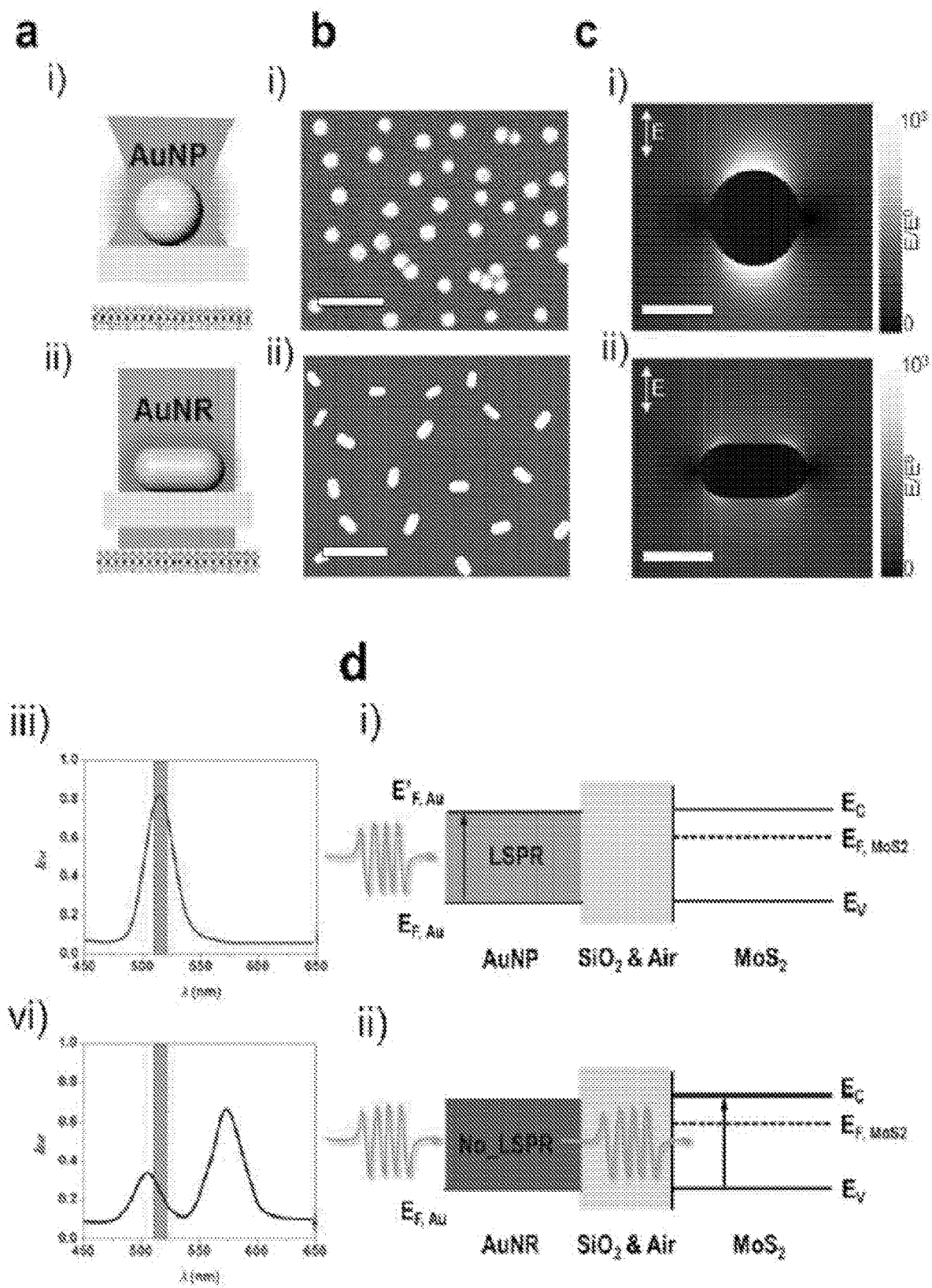
FIG. 2 shows localized surface plasmon resonance (LSPR) induced selective photoenhancement effect on AuNP nanoplasmonic filter and $MoS_2$ photodetector. (a) Plasmonic resonance induces optical filtering effects. (b) Scanning electron microscopy (SEM) image of AuNP and AuNR arrays on SiO2 (scale bar=500 nm), (c) Calculated electric field distribution based on finite element analysis (FEA) reveals high extinction for i) the AuNP and lower extinction for ii) the AuNR with incident light at $\lambda$=532 nm. Extinction peak of iii) the AuNP located at ~532 nm and extinction peaks of iv) the AuNR located at 530 nm and 670 nm. (d) Schematic of the optical filtering mechanism through the $SiO_2$ layer between the AuNP (or AuNR) metal nanostructure and the atomically layered $MoS_2$ (semiconductor) without bandgap bending; i) A LSPR mode in the metal nanostructure enables filtering of the incident light and ii) No LSPR leads to transmission of photons to the atomically layered $MoS_2$, (e) Comparison of photocurrent between the AuNP and the AuNR, (f) nanoplasmonic filtering enhancement as a function of the density of plasmonic particles in the atomically layered $MoS_2$.
Figure 2:
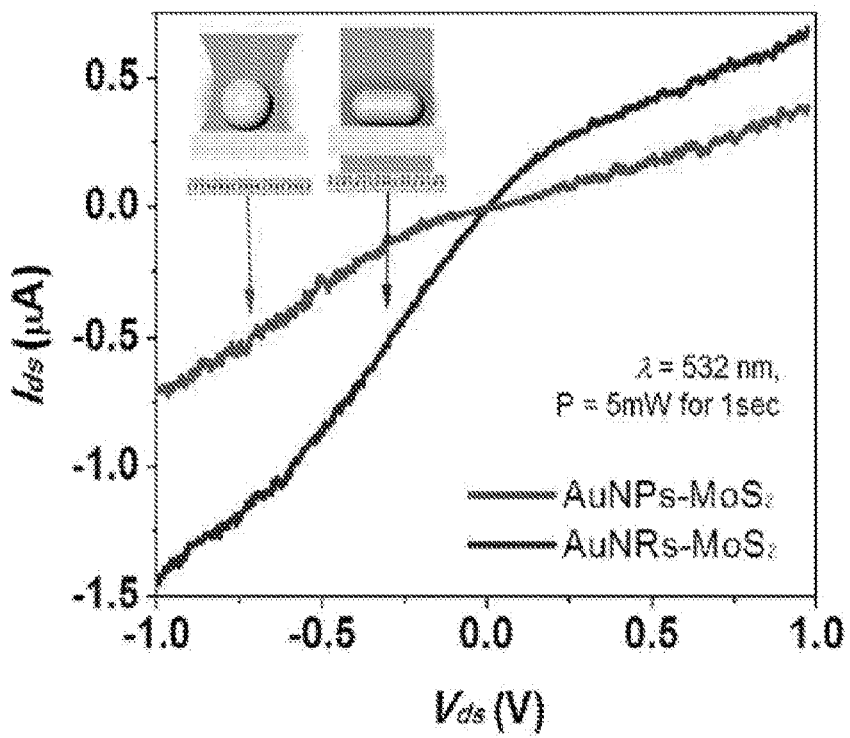
Figure 2:
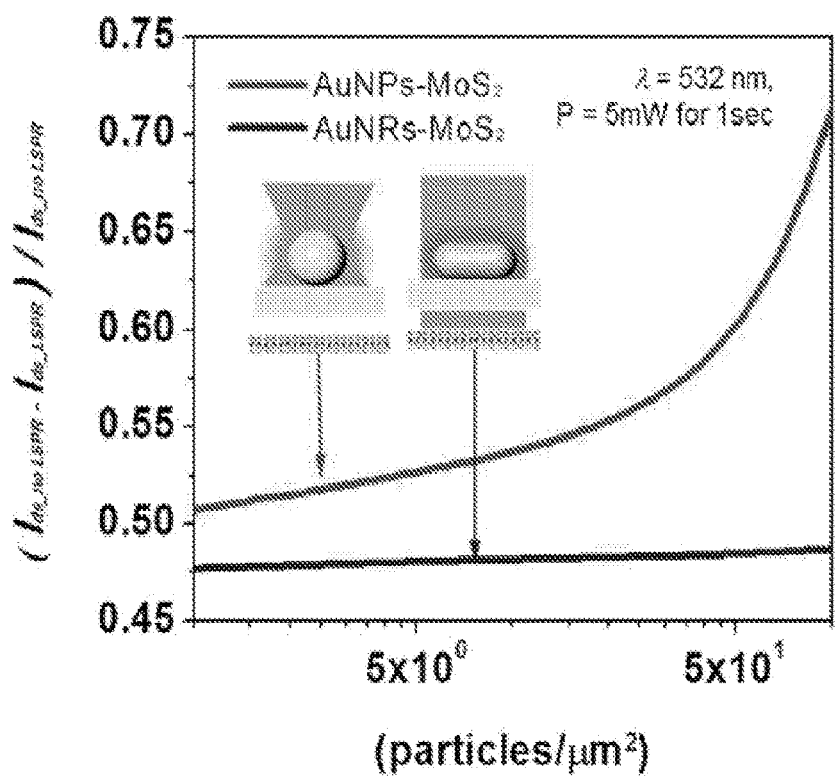

5) Calculation of electric field: Near-field electromagnetic fields around AuNP and AuNR were simulated using a finite element analysis (FEA, COMSOL Multiphysics software) solving Helmholtz wave equation: $\nabla \times (\mu_r^{-1} \nabla \times E) - k_0^2(\varepsilon_r - j\sigma\omega\varepsilon_0)E=0$. Hybrid mesh structures were created for the AuNP and the AuNR to adapt their round shape. The relative permeability and complex permittivity of gold and silver were assumed to be $\varepsilon_r=1$ and $\varepsilon_r=f(\lambda)$, respectively. The polarization vector was applied in the direction parallel to the AuNR structure, whereas the direction of the k-vector was taken to be perpendicular to the plane of the structure. Perfect absorption was assumed at the outer boundary to minimize spurious reflections by setting a perfectly matched layer and an integration layer in concentric space. The dimensions of the AuNP (d=50 nm) and the AuNR (AuNRs (d=40 nm and l=68 nm)) were chosen based on the SEM images as shown in FIG. 2. The surface plasmon of the AuNP is strongly excited at λ=532 nm while the AuNR shows weak excitation at the same wavelength. The adaptive mesh was refined until the maximum electric field converged. Primarily, FEA was used owing to its ability to produce adaptive meshes with high flexibility in geometry. It is more practical than the finite difference time domain (FDTD) method for the complex geometry studied here.

Results

This example describes a cytokine biosensing approach based on a $MoS_2$ photoconductive device that is highly sensitive to light transmission through a biomolecule-capturing nanoplasmonic optical filter. In recent study, photodetectors consisting of a $MoS_2$ layer-based photoconductive channel have been demonstrated as ultrasensitive photoresponse devices (Nam et al., Scientific reports 2014, 5, 10546-10546; Lopez-Sanchez et al., Nat Nano 2013, 8 (7), 497-501; Nam et al., ACS nano 2013, 7 (7), 5870-5881). The approach described herein allows one to take full advantage of high photo-absorption coefficients resulting from the atomically layered structure of $MoS_2$ while avoiding the above-described contact of the photoactive structures with aqueous reagents. This example describes an integrated immunosensor device with a decoupled design that eliminates electron transfer between a nanoplasmonic structure and an atomically layered $MoS_2$ photodetector under light illumination to achieve highly sensitive, rapid, and stable cytokine detection. The nanoplasmonic optical filter of the device is an optically transparent $SiO_2$ layer (170 μm) coated with spherical gold nanoparticles (AuNPs; d=50 nm). Light trapping by the AuNPs due to localized surface plasmon resonance (LSPR) results in an efficient nano optics filtering effect under resonant light illumination (λ=532 nm). The biosensor device is able to detect a pro-inflammatory cytokine, IL-1β, at a concentration as low as 250 fg/mL (14 fM) with a sampling-to-answer time of ~10 min. This LSPR-modulated optoelectronic biosensor finds a wide range of applications, including, but not limited to, point-of-care disease diagnosis, and environmental monitoring.

FIG. 1 illustrates the hybrid integration of a AuNP—$SiO_2$ nanoplasmonic filter layer and a few-layer $MoS_2$ photoconductive flake on a common device platform for cytokine detection. The AuNPs (d=50 nm) on the $SiO_2$ layer are coated with antibodies (Ab) specifically targeting IL-1β. In the absence of the targeted cytokine (IL-1β) molecules, the Ab coated-AuNPs blocks incident light at λ=~532 nm as a result of the LSPR effect ("OFF" mode). In the OFF mode, light transmission through the $SiO_2$ layer becomes weak, keeping incident light from reaching the underlying few-layer $MoS_2$ photoconductive flake. Now, binding of IL-1β molecules onto the Ab-coated AuNP surfaces shifts the plasmonic resonance wavelength owing to a change in the local refractive index near the AuNP surfaces (Chen et al., ACS nano 2015, 9 (4), 4173-4181; Oh et al., ACS sensors 2016, 1 (7), 941-948; Oh et al., ACS nano 2014, 8 (3), 2667-2676). A larger fraction of the incident photons then transmits through the $SiO_2$ thin layer and reaches the underlying $MoS_2$ photoconductive flake ("ON" mode). The ON mode results in a red shift of the extinction spectrum peak of the AuNP—$SiO_2$ nanoplasmonic filter layer, thus leading to an increased photoconduction of the $MoS_2$ flake. The photoconduction of the device is determined by the cytokine concentration of a sample solution deposited on the device surface covered with the AuNP—SiO2 thin layer. Obtaining a correlation between the photoconduction change and the cytokine concentration allows highly sensitive quantification of IL-1β.

FIG. 1b shows a cross-sectional view of the whole decoupled device architecture, where the nanoplasmonic filter and few-layer MoS2 flake are physically decoupled by an intermediate $SiO_2$ thin layer with an air gap. This decoupled architecture ensures non-physical contact between the plasmonic nanostructure and semiconducting structures while other previous device structures incorporated a metal/semiconductor interface (Alicea et al., Nature Physics 2011, 7 (5), 412-417). At the metal/semiconductor interface, it is well known that electron transfer takes place between the plasmonic nanostructure and the few-layer $MoS_2$ flake due to band gap bending. The metal/semiconductor contact device architecture allows direct interaction between plasmonic nanostructure/few-layer $MoS_2$ and biomolecules in an aqueous solution, which leads to non-uniform surface charge distribution and signal instability. In the decoupled architecture, electron transfer causing irradiative plasmon decay is minimized. As such, radiative decay of plasmons in the nanoplasmonic structure only determines the sensitivity of few-layer $MoS_2$ while maintaining high stability of the electrical signal.

The impact of LSPR on the nanoplasmonic filtering effect of the device was tested using gold nanospherical particles (AuNPs) and gold nano nanorod particles (AuNRs) on a $SiO_2$ thin layer. The $SiO_2$ layer was placed on two electrodes adjacent to a few-layer $MoS_2$ photoconductive film, which were connected to electronics used to characterize the device. One of the gold electrodes acting as a drain was connected to a voltage source while the other, the source electrode, was grounded (FIG. 1b, FIG. 2 and Methods). The testing structures were prepared by attaching nanoparticles to a 3-Aminopropyl triethoxysilane (APTES)-functionalized SiO2 thin layer with an amino functional group. The resulting AuNP and AuNR structures on the $SiO_2$ thin layer revealed uniform color over ~5 $mm^2$ area samples, which showed uniform distribution of the nanoparticles on the surface. The morphology and optical property of each testing structure were analyzed by scanning electron microscopy (SEM), and ultraviolet-visible (UV-VIS) spectrometer. It was verified that a monolayer of AuNPs or AuNRs was uniformly distributed on the $SiO_2$ thin layer without aggregations for each structure. Same particle density of the AuNPs and AuNRs (FIG. 2b, $d_{particle}$=~25 particles/$\mu m^2$) were tested.

Figure 5:
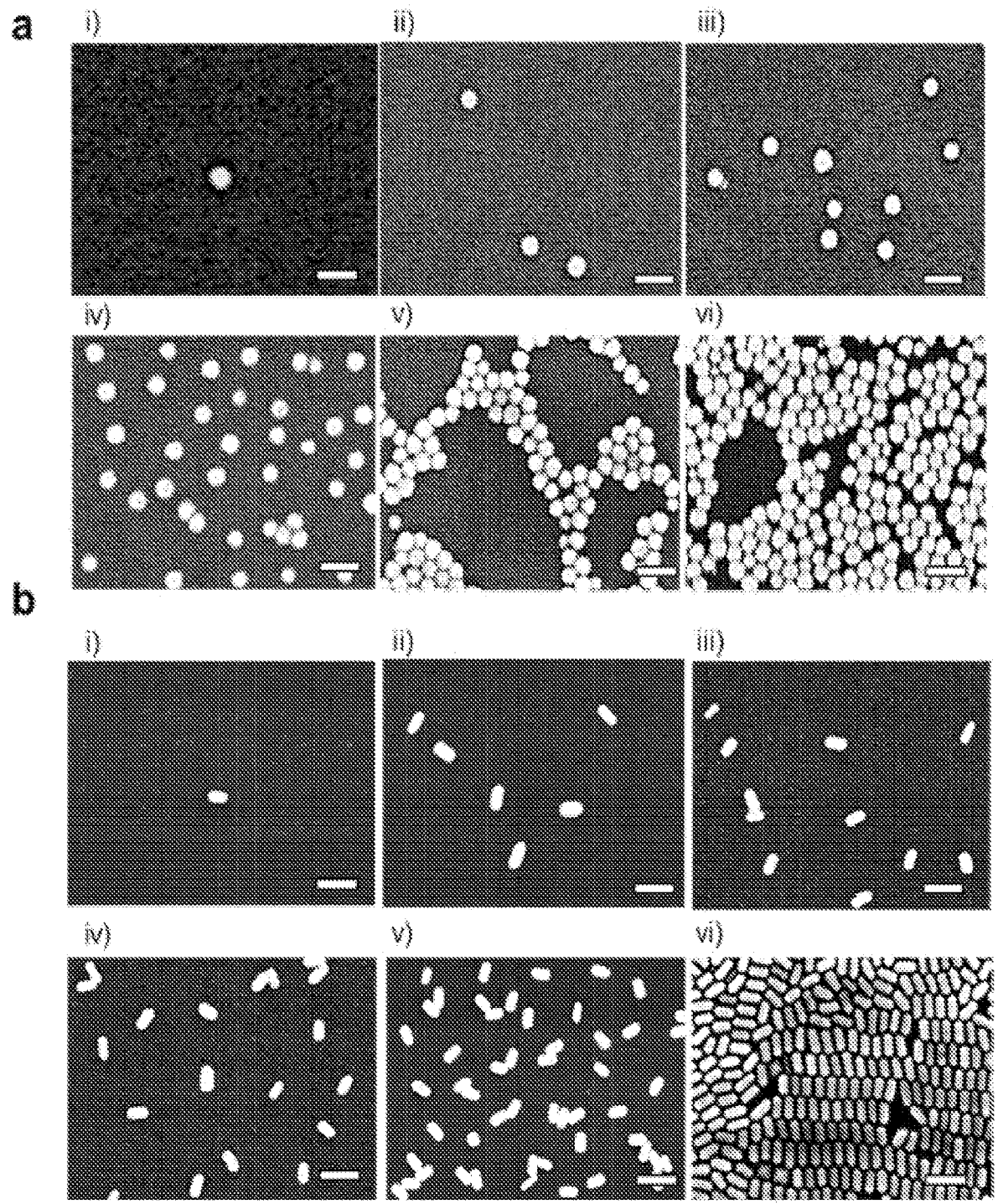
FIG. 5 shows morphologies of plasmonic nanoprobes of gold nanospherical particles (AuNPs) and gold nanorod particles (AuNRs) taken by scanning electron microscopy (SEM) with varying particle density on $SiO_2$ substrate. (a) SEM images of AuNPs with i) ~1 particle/µm², ii) ~5 particles/µm², iii) ~10 particles/µm², iv) ~25 particles/µm², v) ~50 particles/µm², and vi) ~200 particles/µm² and (b) Optical properties of AuNRs with i) 1 particle/µm², ii) ~5 particles/µm², iii) ~10 particles/µm², iv) ~25 particles/µm², v) ~50 particles/µm², and vi) ~200µ particles/µm².
Figure 6A:
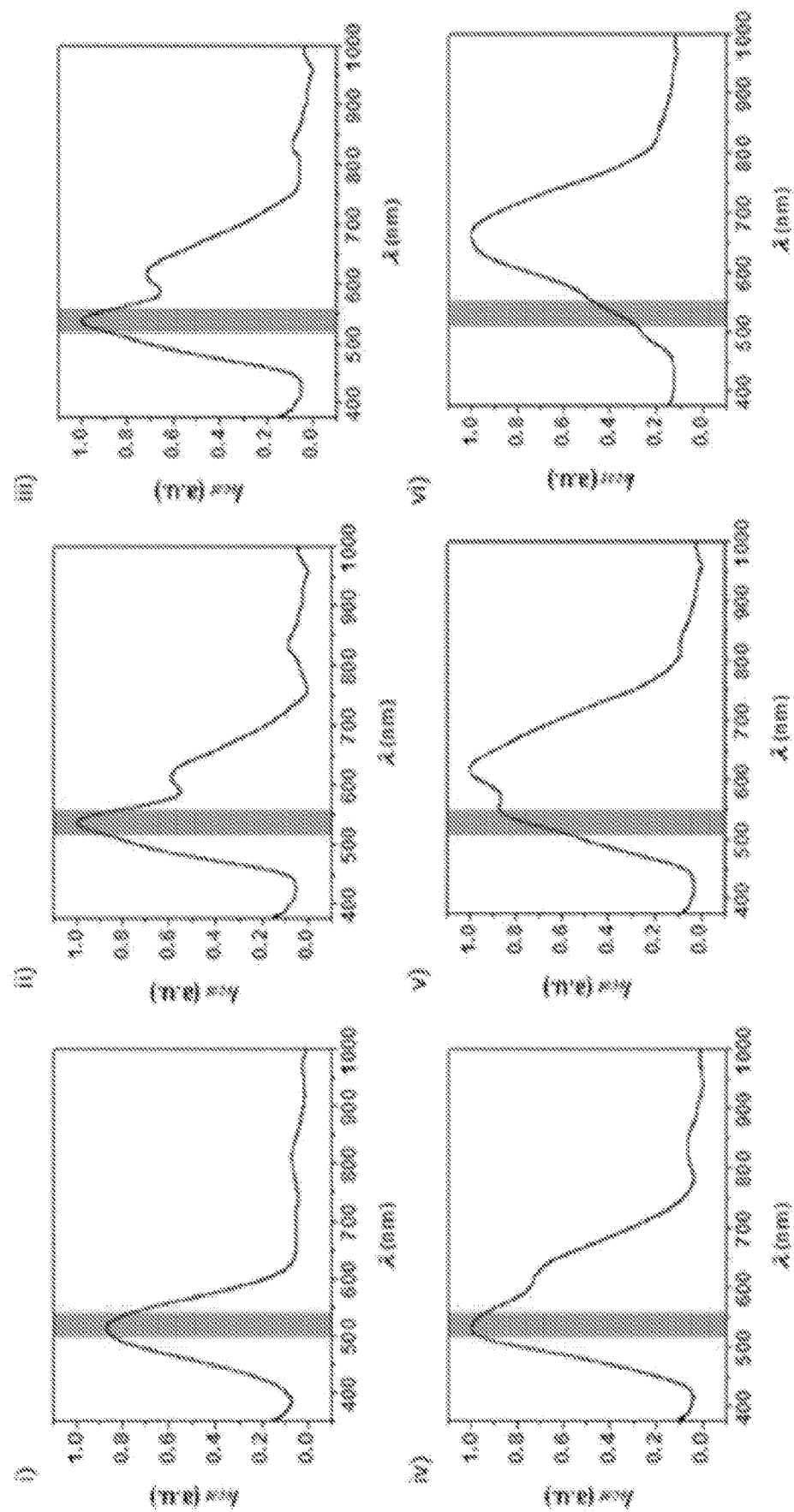
FIG. 6 shows optical properties of nanoplasmonic optical filter with varying particle density on $SiO_2$ substrate. (a) Optical properties of AuNPs with i) ~1 particle/µm², ii) ~5 particles/µm², iii) ~10 particles/µm², iv) ~25 particles/µm², v) ~50 particles/µm², and vi) ~200 particles/µm² and (b) Optical properties of AuNRs with i) 1 particle/µm², ii) ~5 particles/µm², iii) ~10 particles/µm², iv) ~25 particles/µm², v) ~50 particles/µm², and vi) ~200 particles/µm².
Figure 6B:
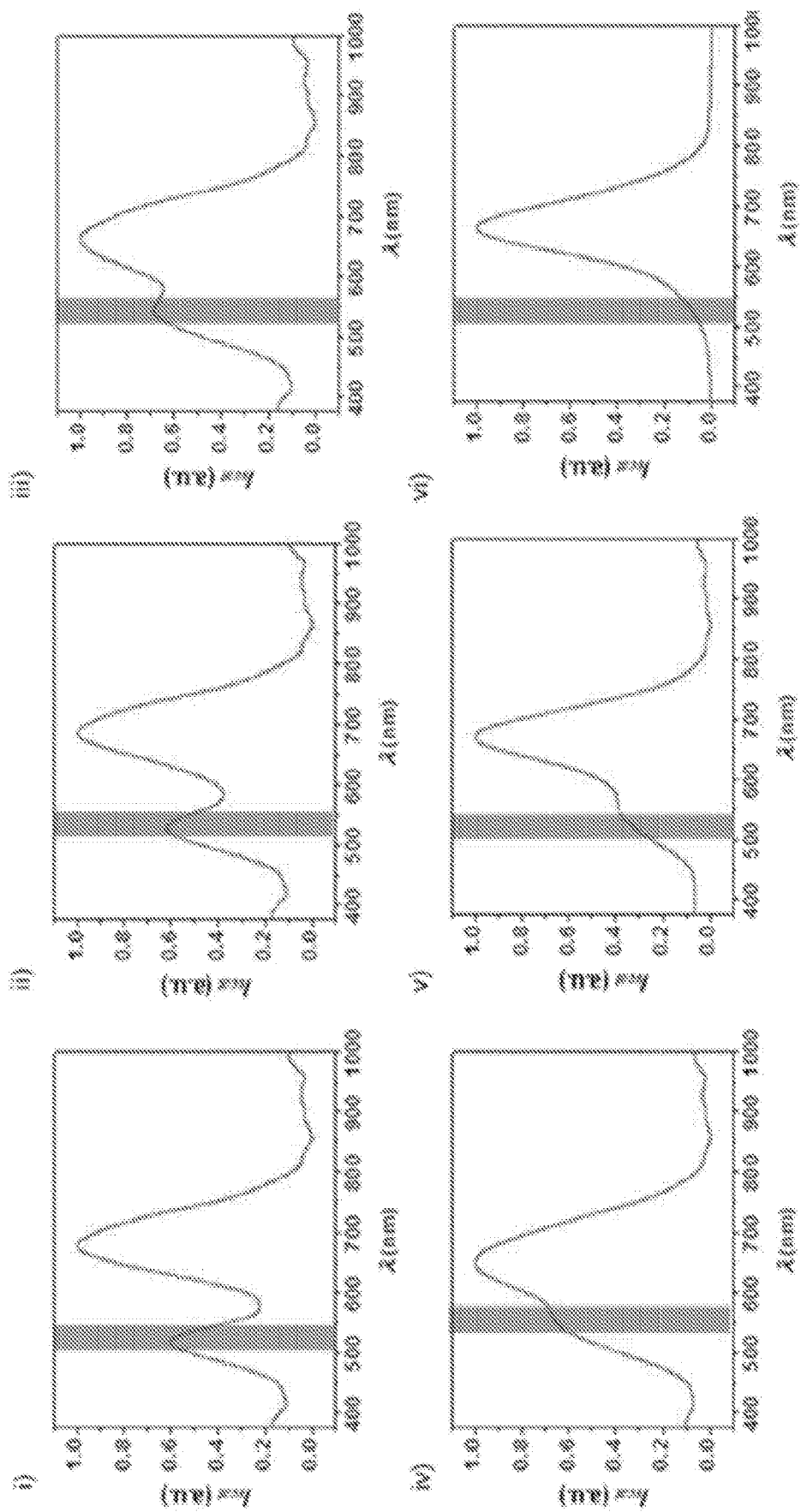

The test used a laser light source with λ=532 nm±10 nm light. It is known that the AuNPs (d=50 nm) exhibit strong LSPR at this wavelength while the plasmonic resonance peak of the AuNRs (d=40 nm and l=68 nm) lies at λ=630 nm. Calculated electric field distributions around AuNP and AuNR support the high extinction in AuNP (FIG. 2c). It was hypothesized that the plasmonic filtering effect would cause the AuNPs to yield a lower photo current signal in the few-layer $MoS_2$ flake than the AuNRs (FIG. 2d). The photoconduction experiment was performed for devices incorporating the testing structures above (FIG. 2e). The test obtained a photocurrent of $I_{ds}$=0.21 μA at a drain-source voltage of Vds=1.0 V and Ids=−0.7 μA at Vds=−1.0 V with the AuNPs, whereas Ids=0.75 μA at Vds=1.0 V and Ids=−1.5 μA at Vds=−1.0V with the AuNRs. Indeed, these experimental results verified the hypothesis. A five times greater plasmonic filtering effect with the AuNPs than with the AuNRs was observed, which indicates that strong extinction-based resonance between plasmonic nanoparticle and incident light determines the performance of the nanoplasmonic filter. In addition, the density of AuNPs was controlled on $SiO_2$, expecting that it would tune the filtering intensity under the resonance condition. Here, testing structures were prepared with 6 different densities of AuNPs and AuNRs on a SiO2 thin layer: ~1, ~5, ~10, ~25, ~50, and ~200 particles/μm². Regardless of the density of the nanoparticles except for ~200 particles/μm², the peak locations of the strong extinction were consistent across all the structures for both AuNPs and AuNRs. A density higher than ~200 particles/μm² causes interparticle plasmonic coupling induced by an increase in the refractive index (FIGS. 5 and 6), which results in a broader spectrum of the extinction peak. To quantify the plasmonic filtering effect, nanoplasmonic filtering enhancement was defined as $(I_{ds\_no\ LSPR} - I_{ds\_LSPR})/I_{ds\_no\ LSPR}$, where $I_{ds\_no\ LSPR}$ is photocurrent without plasmonic nanoparticle and $I_{ds\_LSPR}$ is photocurrent with plasmonic nanoparticles). The nanoplasmonic filtering enhancement with the nanoparticle density shown in FIG. 2f is further evidence supporting the mechanism of the nanoplasmonic filter. The nanoplasmonic filtering variation from AuNPs dramatically increased from ~0.50 to 0.75 with particle density changes from 1 to 50 particles/μm2, while the change of photocurrent from AuNRs was from 0.47 to 0.48 with a similar range of particle density change in AuNPs.

Figure 3:
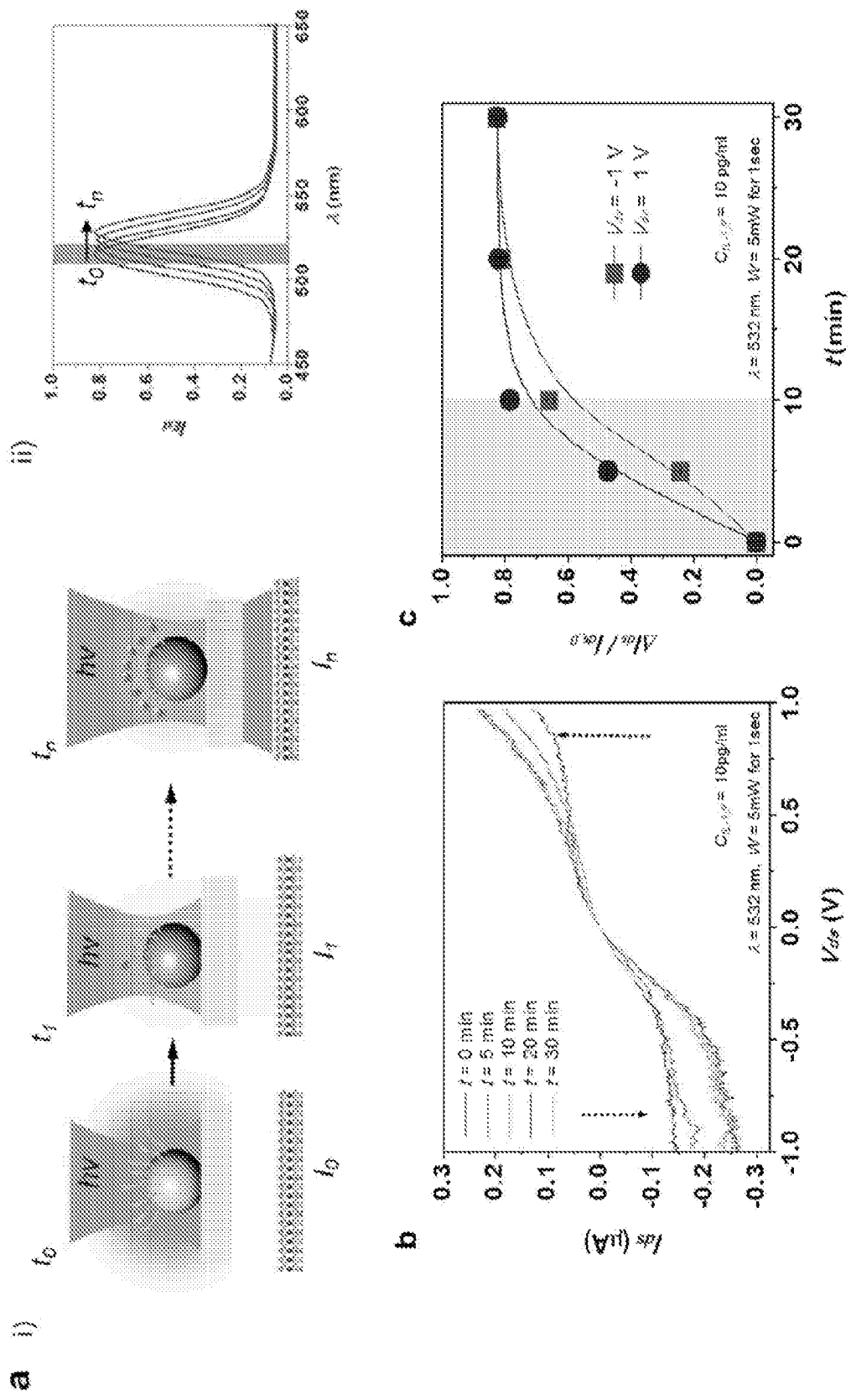
FIG. 3 shows rapid detection performance of bio-tunable nanoplasmonic filter on few-layer $MoS_2$ photodetector. (a) IL-1β surface binding effect on photo transmission of nanoplasmonic filter over time; (b) $I_{ds}$ vs. $V_{ds}$ curves of the few-layer $MoS_2$ photodetector at different IL-1β surface binding incubation time points for a fixed IL-1β concentration of C IL-1β=10 pg/ml. (c) photocurrent variation over time during incubation process at Vds=1.0 and −1.0 V for C IL-1β=10 pg/ml.

Next, rapid detection of cytokines was performed with the devices. The study employed interleukin-1 beta (IL-1β), a pro-inflammatory cytokine, in an aqueous phase as a model analyte. IL-1β was chosed as the target because of (i) its clinical significance in immune monitoring processes (Masters et al., Annual review of immunology 2009, 27, 621) (ii) the well-developed binding chemistry between IL-1β and its antibody on gold nanoparticles (FIG. 1), and (iii) its surface binding that causes a near-field refractive index change without causing optical interference (Haes et al., Journal of the American Chemical Society 2002, 124 (35), 10596-10604; Jung et al., Langmuir 1998, 14 (19), 5636-5648; Willets et al., Annu. Rev. Phys. Chem. 2007, 58, 267-297). The biosensor preparation involved: (i) immobilization of gold nanoparticles onto a $SiO_2$ thin layer (AuNPs/$SiO_2$), (ii) self-assembly of 1-ethyl-3-[3-dimethylaminopropyl] carbodiimide (EDC) and/N-hydroxysuccinimide (NHS) on the particle surfaces, (iii) antibody conjugation on the functionalized particles (Ab-AuNP/$SiO_2$), and (iv) attachment of the Ab-AuNP/$SiO_2$ thin layer on a few-layer $MoS_2$ flake with an alignment mark. The Ab-AuNP conjugate (50 nm in diameter) scatters light at λ=532 nm with a sufficient intensity. The measured photocurrent (Ids) increases over time with cytokine-antibody binding progresses on a nanoparticle surface. Here, a local refractive index change accompanying the cytokine binding causes a red shift of the extinction peak of the particle, leading to higher light transmission through the nanoplasmonic filter (FIG. 3a). After loading IL-1β($C_{IL-1β}$=10 pg/mL) in a Phosphate-buffered saline (PBS) solution followed by a 30-min incubation process, the photo response of the device to a light illumination was measured as a function of time (method) (FIG. 3b). At t=0 min, the photocurrent Ids was ~0.11 μA at Vds=1.0 V. The Ids at Vds=1.0 V increased two times to ~0.23 μA in 10 min during the incubation process and reached a plateau later with the IL-1β-anti-IL-1β binding equilibrium established on the AuNPs of the nanoplasmonic filter. The plot of $I_{ds}$ over time ($I_{ds}$-time curve) represents the IL-1β binding kinetics and allows us to estimate the binding affinity of IL-1β. The attachment and detachment rates of IL-1β were obtained from curve fitting to the plot based on a standard 1:1 binding kinetics model as $k_{off}$=4.2×10$^{-5}$ M$^{-1}$ sec$^{-1}$ and $k_{on}$=2.9×10$^5$ M$^{-1}$ sec$^{-1}$, respectively. The equilibrium constant ($K_{eq}$) was estimated to be 6.9×10$^9$ M$^{-1}$, which well matches a typical equilibrium constant value for an antigen-antibody interaction. With 5 repeats of the measurement, good repeatability of the biosensing performance of the device was obtained. One would expect shorter detection time to determine the concentration of IL-1β using the subthreshold regimes analysis in the few-layer MoS2 thin-film transistors (Nam et al., Scientific reports 2014, 5, 10546-10546). The $I_{ds}$ variation ($\Delta I_{ds}/I_o$)-time curves with a light illumination reached a steady state in ~10 min (FIG. 3c). Both at $V_{ds}$=1.0 and -1.0 V, the time for the steady state is similar. Regardless of $V_{ds}$=1.0 and -1.0 V, the ΔIds/Io shows consistent value (=0.8) at the steady state.

Figure 4:
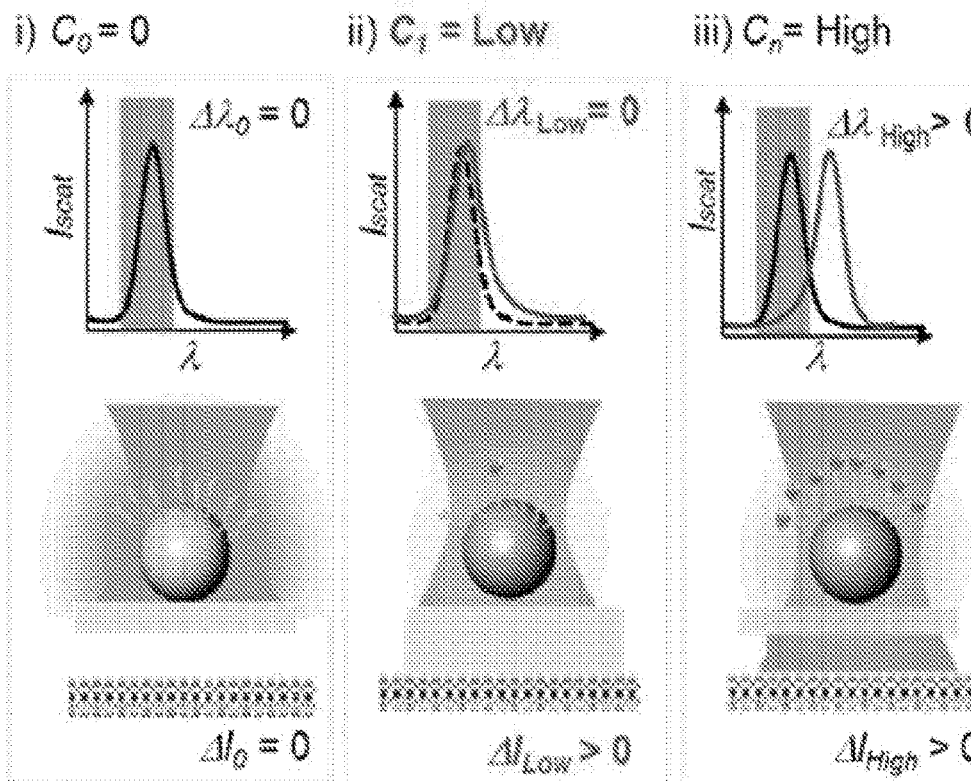
FIG. 4 shows IL-1β sensitivity of bio-tunable nanoplasmonic filter on few-layer $MoS_2$ photodetector. (a) Illustration of highly sensitive IL-1β detection using few-layer $MoS_2$. (b) LSPR spectra of AuNP coated $SiO_2$ surface at C IL-1β ranging from 0.1 pg/mL to 1 ng/ml, (c) Photocurrent variation during IL-1β surface binding incubation for different C IL-1β values.
Figure 4:
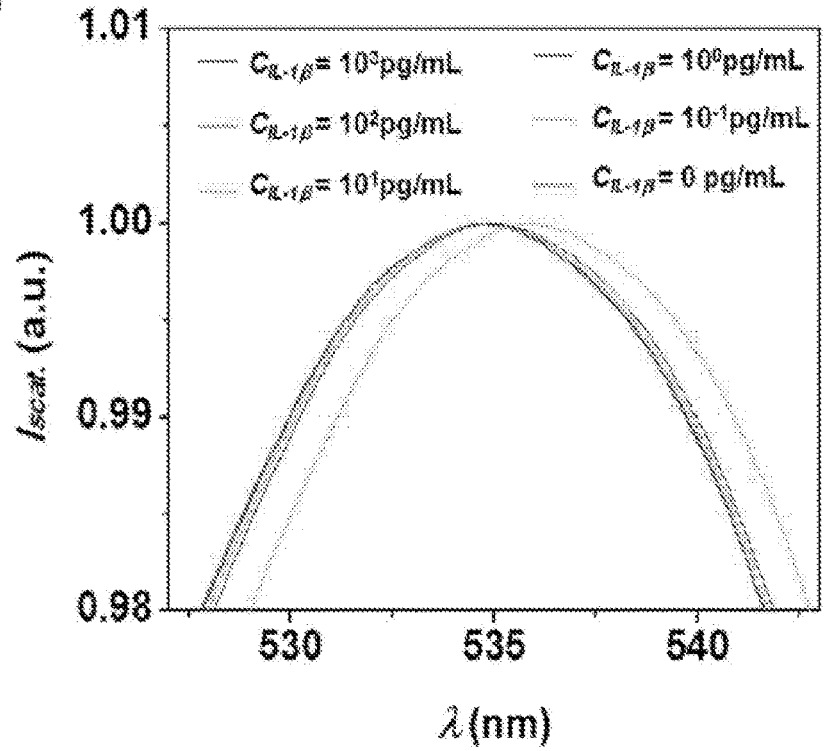
Figure 4:
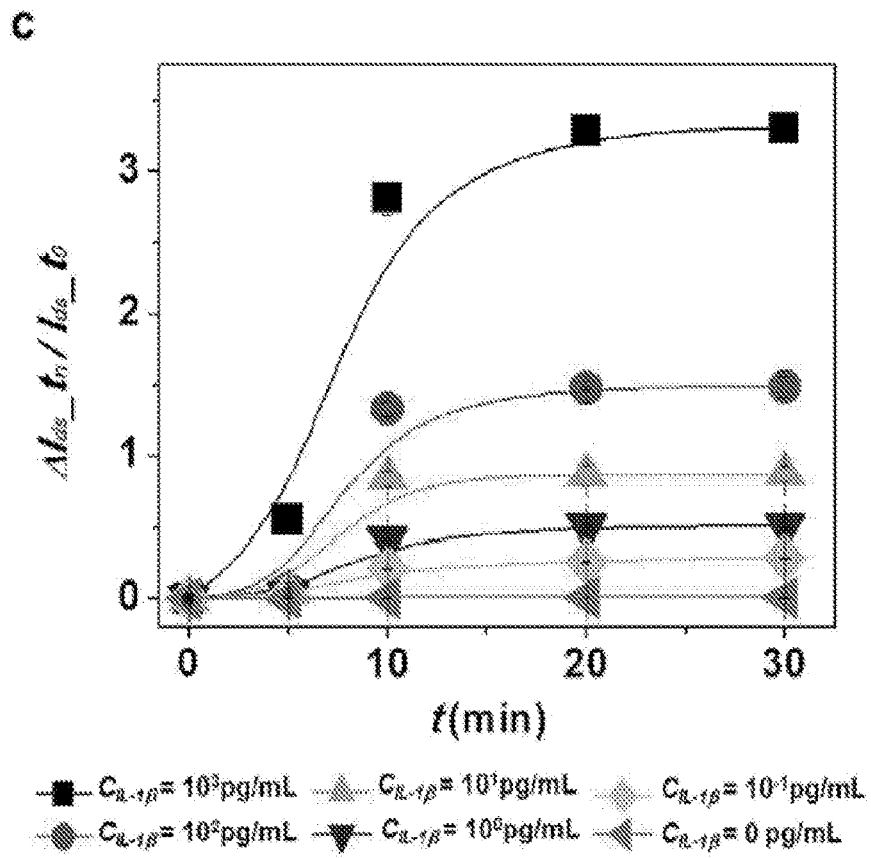
Figure 4:
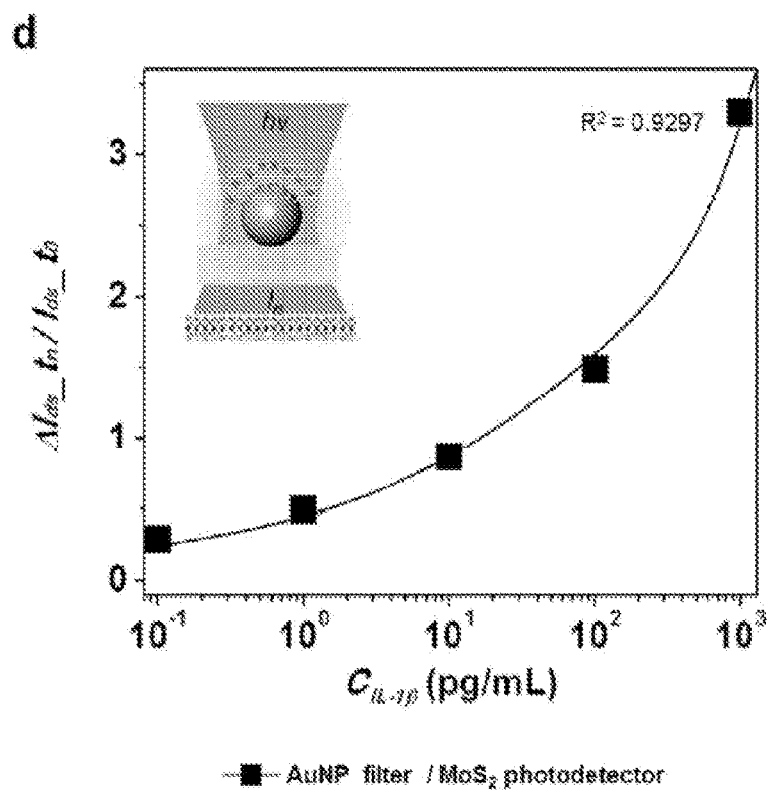

The cytokine measurement was performed with different concentrations of IL-1β from 0.1 pg/mL to 1 ng/mL (FIG. 4). Varying the concentration of IL-1β is expected to change the overlapping spectral band between the extinction peak of the nanoparticle and the wavelength of the light source. Increasing the IL-1β concentration results in higher optical transmission, leading to an increase in the photocurrent of the device (FIG. 4a). Measuring the photocurrent changes allowed one to quantify the IL-1β concentration of a sample. The biosensor device incorporating the high-sensitivity few-layer $MoS_2$ photoconductive thin layer enabled recognition of a very low light intensity change at the presence of low-concentration IL-1β. Initial measurements measured the LSPR extinction spectral peak shift of the Anti-AuNP/$SiO_2$ thin layer from $C_{IL-1β}$=0.1 pg/mL to $C_{IL-1β}$=1 ng/mL using a photo spectrometer (USB4000, Ocean Optics) (Oh et al., ACS sensors 2016, 1 (7), 941-948; Oh et al., ACS nano 2014, 8 (3), 2667-2676). The measured peak shift was ~0 or 0.2 nm (FIG. 4b), which was too small to detect with the above-mentioned LSPR extinction spectrum detection setup. However, the device described herein allowed quantification of IL-1β at a low concentration by managing to detect the subtle LSPR peak shift. At $V_{ds}$=1V, $I_{ds}$ increases from ~0.15 μA to 0.45 μA with CIL-1β increasing from 0.1 pg/mL to 1 ng/mL. The $I_{ds}$-time curves across the measured range of CIL-1β reached a steady state in ~10 min as was observed in FIG. 3c. FIG. 4c clearly demonstrates that the device yields high cytokine detection sensitivity. The sensitivity of the biosensor (LSPR/$MoS_2$) was compared to the commercial photospectrometer detecting an extinction spectral shift (LSPR) at the same surface density of AuNP on $SiO_2$ as a function of IL-1β concentration. In the comparison, the limit of detection from the decoupled LSPR/$MoS_2$ ($LOD_{LSPR/MoS2}$) from the obtained calibration curve (FIG. 4d), the device achieved a $LOD_{LSPR/MoS2}$ of 0.25 pg/mL while the direct LSPR extinction peak shift detection obtained a $LOD_{LSPR}$ of 22.5 pg/mL at the same density of AuNPs. Here, all the LOD values were given by 3σ/kslope, where 6 and kslope are the standard deviation of background signal measured from a blank control and regression slope of calibration curve, respectively. The decoupled LSPR/$MoS_2$ device is ~90 times higher sensitive in comparison to AuNPs based LSPR detection method. The LODLSPR/$MoS_2$ and time range of the LSPR/$MoS_2$ biosensor are comparable to the gold standard, ELISA. Highly sensitive plasmonic nanostructure such as AuNRs resulted in lower LODLSPR for better cytokine detection capability. In this consideration, the decoupled integration of highly sensitive plasmonic nanostructures in the LSPR/$MoS_2$ biosensor allows one to achieve higher sensitivity.

In conclusion, the example describes a high-sensitivity, label-free cytokine immuno biosensing device integrating AuNP plasmonic biosensing assemblies on a SiO$_2$ thin layer and a MoS$_2$ photoconductive flake. The binding of biomolecules at the surfaces of antibody-conjugated AuNPs changed the extinction spectrum peak of the SiO$_2$ thin layer due to a LSPR peak shift between the AuNPs and incident light. This effect enabled the AuNP—SiO$_2$ thin layer to act as a tunable optical filter responding to the presence of cytokines in a solution deposited on the device surface. The unique device architecture prevented electronic interactions between the photo-excited AuNP assemblies and semiconducting MoS$_2$ with a physical gap. This arrangement enabled highly stable detection of subtle variations of photocurrent in the MoS$_2$ layer accompanying changes in the light transmission of the AuNPSiO$_2$ film during biomolecule quantification in an aqueous solution. As a result, it was possible to detect IL-1β in PBS at a concentration as low as 250 fg/mL (14 fM) while obtaining its surface binding curve. Real-time monitoring of the binding curve enabled the analysis to be completed within 10 min without waiting for the biosensing process to reach an equilibrium state. The plasmo-photoelectronic biomolecule detection approach demonstrated in this study makes the device highly poised for standalone operation and clinically relevant point-of-care applications.

TABLE 1

Limit of detection (LOD) resulting from different cytokine detection methods. A LOD value was determined for three cytokine detection methods, given by $3\sigma/k_{slope}$, where $\sigma$ is the standard derivation of background noise detected from a blank sample, and $k_{slope}$ is the regression slope extracted by sigmoidal curve-fitting from a standard curve.

| | Blank S.D. ($\sigma$) (%) | $U_{system}$ ($3\sigma$) (%) | $k_{slope}$ (pg/mL)−1 | LOD = $3\sigma/k_{slope}$ (pg/mL) |
|---|---|---|---|---|
| LSPR/MoS$_2$ | $4.61 \times 10^{-4}$ | $1.38 \times 10^{-3}$ | 0.0035 | 0.25 |
| LSPR | $1.50 \times 10^{-3}$ | $4.50 \times 10^{-3}$ | 0.0002 | 22.5 |
| ELISA | 0.0135 | 0.0405 | 0.004 | 10.12* |

Example 2

This example describes a wearable label-free cytokine biosensor that can continuously monitor immune status of subjects.

Plasmonic Nano Antenna/MoS$_2$ Biosensor: As discussed above (Example 1), 2D materials (MoS$_2$) are useful as active biosensor elements because of their highly sensitive photo detection capability and mechanical flexibility. A highly sensitive and rapid cytokine biosensor was developed integrating together a nano plasmonic optical filter and a highly sensitive MoS$_2$ photodetector showing stable sensing capability. The nanoplasmonic optical filter of the device includes anti-cytokine antibody-conjugated plasmonic nano antenna arrays (AuNS) on a SiO$_2$ dielectric thin film suspended above a few layers of photoactive 2D MoS$_2$ with a few tens of μm gap (Example 1). The device detected proinflammatory IL-1β cytokine at a concentration as small as 1.0 pg/mL within 10 min in a label-free manner (Example 1).

Tunable Plasmonic Nanoantenna Synthesis (Co-Block Polymer Based Self-Assembly): Plasmonic nano antenna biosensor structures are widely used in optofluidic devices for highly sensitive detection and analysis of biomedical and environmental samples. However, up to date, the uncontrolled size of nano feature, poor uniformity, and low density of the plasmonic nanostructure arrays have resulted in the low sensitivity and narrow dynamic range of these biosensors.

Figure 9:
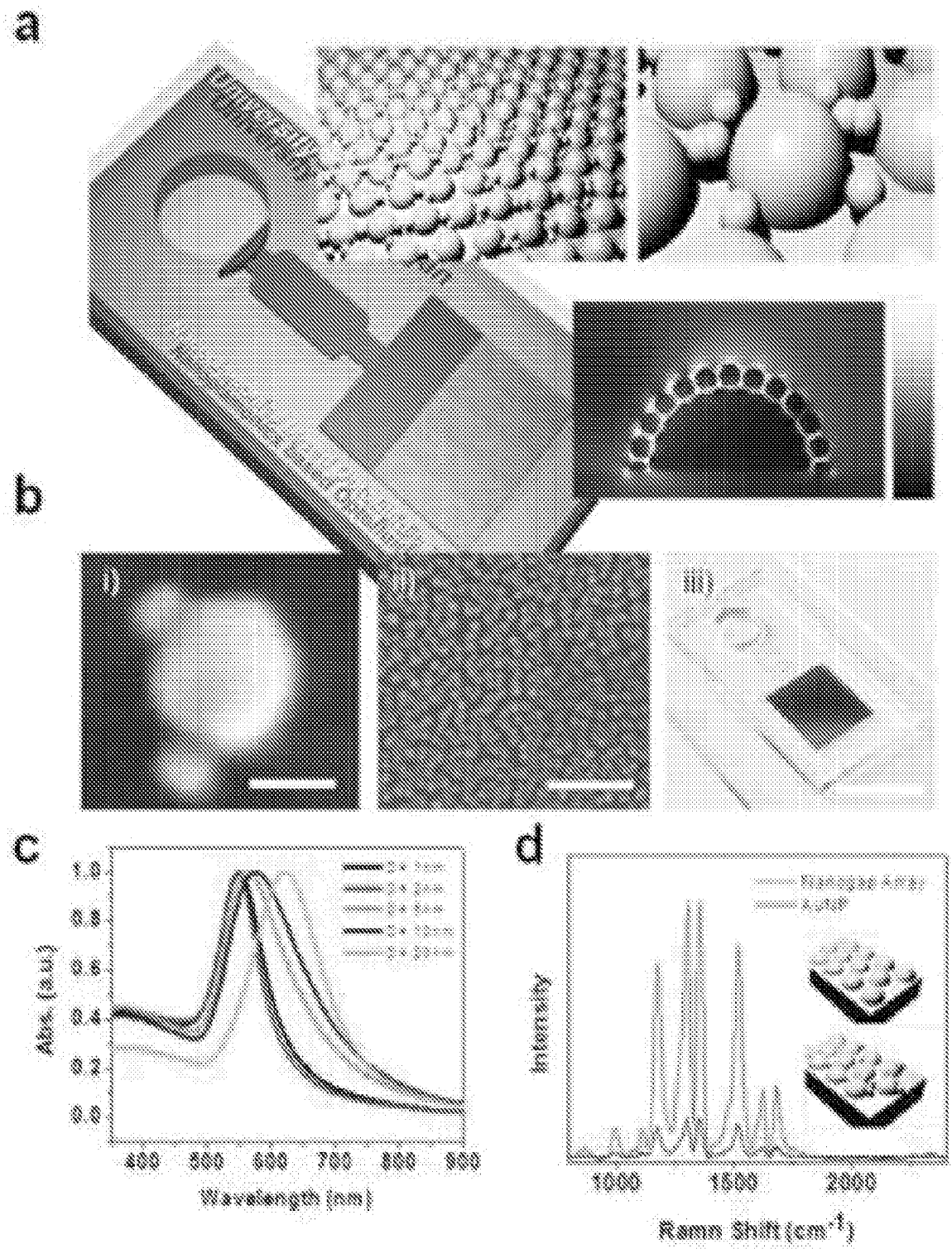
FIG. 9 shows high uniform and density of integrated nano plasmonic gap array with sub-nanometer feature. (a) Schematics of microfluidic device integrating plasmonic nano antenna arrays with satellite branches filling their gaps (b) Nano antenna array images: i) SEM images of single plasmonic nano antenna structure (scale bar=25 nm), ii) SEM images of arrays of the plasmonic nano antenna structure (scale bar=100 nm) and iii) Photo image of nano antenna array-integrated microfluidic device. (c) Nano antenna array LSPR spectral peaks for varying average size of satellite dots. (d) Raman spectrum enhancement of plasmonic nano antenna arrays due to gap-filling satellite branches (e) Obtained plasmonic nano antenna; i) high density of plasmonic nano antenna arrays, ii) highly ordered plasmonic nano antenna arrays, iii) plasmonic nano antenna arrays with satellite branches of sub-nano features, iv) fully overgrown plasmonic nano antenna, v) asymmetric plasmonic nano antenna and vi) asymmetric plasmonic nano antenna with sub nano branches (scale bar=100 nm).
Figure 9:
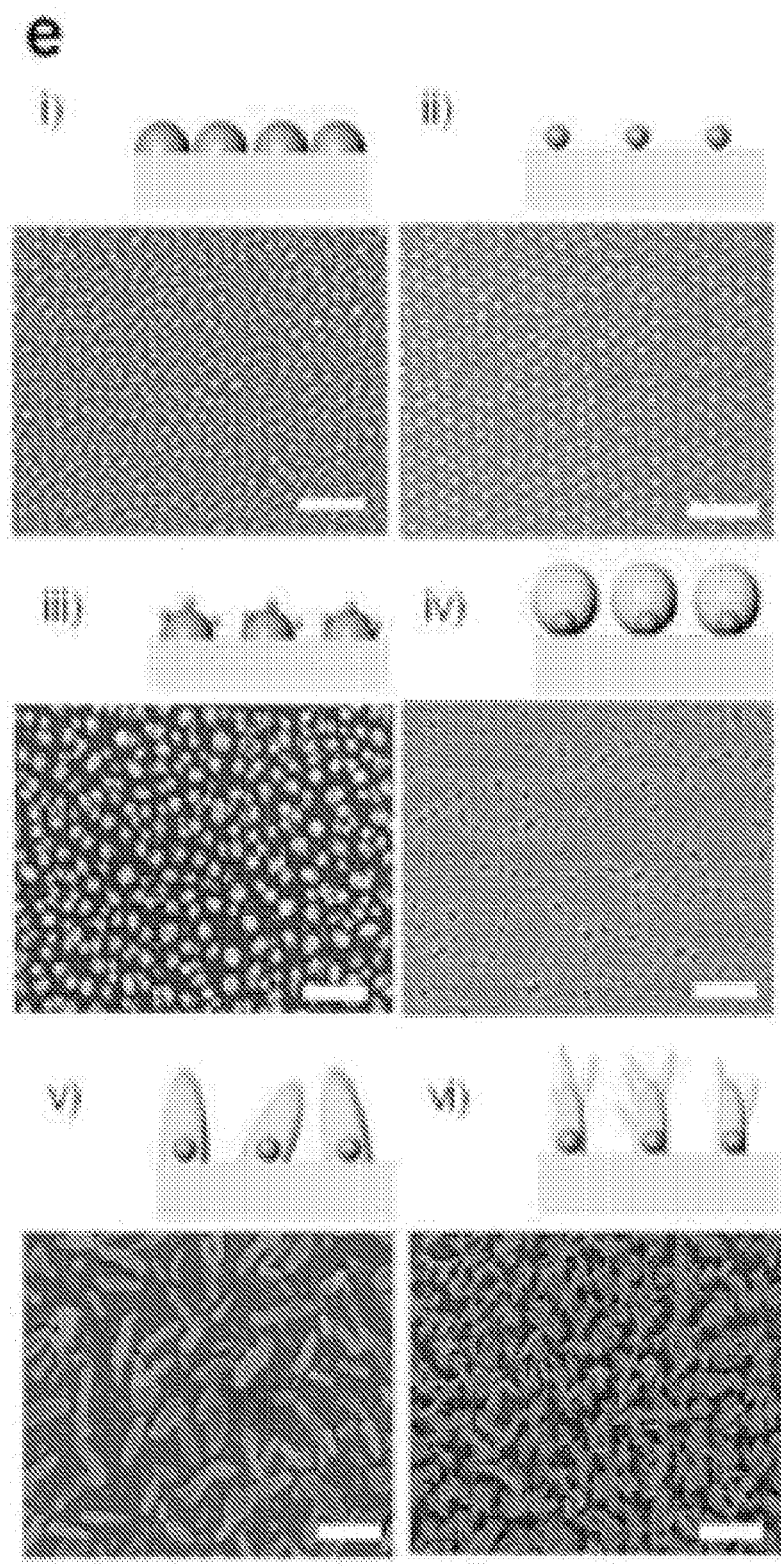

To address these issues, this example developed a new nanomaterial synthesis technique yielding high-density plasmonic nano antenna arrays on a substrate, whose array-to-array gaps are filled with satellite branches of sub-nanometer features (FIG. 9). The satellite branches significantly enhance the localization of EMs upon interaction with incident light, which leads to high-sensitivity LSPR sensing. More specifically, the high-density plasmonic nano antenna arrays were constructed by dewetting and building-block self-assembly. The satellite branches between the plasmonic nano antenna arrays on flexible arrays were formed by consecutive chemical overgrowth. A systematic optical characterization revealed that strong LSPR extinction peaks resulted from the satellite branches, which represented ~10$^3$ times enhanced focusing of EMs in the visible regime. The extinction peaks can be readily tuned by varying the satellite branch size and the nano gap distance. In addition, a surface enhanced Raman scattering (SERS) measurement shows that ~10$^2$ times higher sensitivity can be achieved with these nano antenna arrays for detection of a standard molecule (R6G) than conventional nano antenna structures consisting of gold spherical nanoparticles.

High-sensitivity MoS$_2$ photodetectors on a flexible substrate: Nanoprinting techniques and highly efficient MoS$_2$ photodiodes are used to produce integrated arrays of highly sensitive MoS$_2$ photodetectors on flexible substrates. These photodetector arrays are anticipated to have a high uniformity in their photo response parameters, such as short-circuit photocurrent (Isc), open-circuit voltage (Voc), and responsivity. The relative detector-to-detector variation of these parameters is expected to less than 10% over the whole chip. In addition, such photodetector arrays can be easily integrated with plasmonic nanoantenna biosensor structures as well as I/O circuits for enabling fast sensor reading.

A nanoprinting method capable of integrating pre-patterned MoS$_2$ nano/microstructures in active device sites on hosting substrates or circuits is employed. FIG. 10 illustrates the nanoprinting method, which is termed as Nanoimprint-Assisted Shear Exfoliation plus Transfer Printing (NASE+ TP). Before a NASE+TP process, a MoS$_2$ stamp bearing protrusive mesas is fabricated using photolithography followed by plasma etching (FIG. 10a). Here, the periodic mesas are pre-patterned photoactive structures for making the photodetectors. The mesa heights (the photoactive layer thickness) is well controlled by the etching time. This MoS$_2$ stamp is subsequently used to perform a NASE process (Chen et al., ACS Nano, 2015, 9, (9), pp. 8773-8785). Specifically, the MoS$_2$ stamp is mechanically pressed against an elastic polydimethylsiloxane (PDMS) substrate through a nanoimprint lithography (NIL) process, and the protrusive mesas on the stamp are mechanically embedded into the PDMS substrate (FIG. 10b). After the imprint step, a lab-made shear-strain generation tool is used to generate a shear displacement between the imprinted mesa features and the stamp (FIG. 10c). Due to this shear displacement, the imprinted mesa structures can be exfoliated away from the stamp along the shear direction (FIG. 10c). After this shear exfoliation step, the imprint stress is released, and the MoS$_2$ stamp is separated from the PDMS substrate. Due to the elasticity of PDMS, the surface of the PDMS substrate can quickly restore back to its original flat morphology, and the exfoliated MoS$_2$ photoactive layers are lifted up to the flat surface of the substrate (FIG. 10d). In a NASE process, the thicknesses of exfoliated MoS$_2$ layers are mainly determined by the imprinting depth (or pre-defined height) of the mesas (Chen et al., ACS Nano, 2015, 9, (9), pp. 8773-8785). In this example, the $MoS_2$ or other TMDC flake thickness is controlled to be in the range of 150-200 nm, which results in the highest optical responsivity (photocurrent per incident light power) (Wi et al., ACS Nano, 2014, 8, (5), pp. 5270-5281; Wi et al., Appl. Phys. Lett., 2014, 104, pp. 232103/232101-232103/23210; Chen et al., Appl. Phys. Lett., 2013, 103, (14), pp. 142110/142111-142110/142114). After the NASE step, the PDMS substrate bearing asexfoliated $MoS_2$ pixels (or photoactive layer arrays) serves as a transferring stamp for transfer-printing the $MoS_2$ pixel arrays onto the final device substrate (the flexible polymeric substrate bearing pre-fabricated I/O circuits) (FIG. 10e). Especially, before this transfer-printing process, metal-based I/O circuit structures or arrays with the same pattern lay-out as that of $MoS_2$ mesas (or photoactive layer arrays) has been pre-fabricated on the target flexible substrate. Such metal circuit structures can serve as very effective adhesion layers for fixing printed $MoS_2$ flake pixels. During a transfer-printing step, the $MoS_2$ mesa patterns on the PDMS stamp are precisely aligned with the circuit structures on the target substrate using a moving stage system under an optical microscope, and then they are pressed against the target substrate. Afterwards, the PDMS substrate is heated up to 90-120° C. (FIG. 10e), and the $MoS_2$ structures are thermally released from the PDMS stamp and transferred onto the target substrate (FIG. 10f). The printed $MoS_2$ structure arrays are further tailored into photodetector architectures. Specifically, arrays of three types of $MoS_2$-based photodetectors, including (a) plasma-doped pn-junction detectors (Wi et al., ACS Nano, 2014, 8, (5), pp. 5270-5281; Wi et al., Appl. Phys. Lett., 2014, 104, pp. 232103/232101-232103/23210; Chen et al., Appl. Phys. Lett., 2013, 103, (14), pp. 142110/142111-142110/142114), (b) $MoS_2$/WSe2 heterojunction detectors (Wi et al., J. Vac. Sci. Technol., B, 2016, 34, pp. 06KA01), and (c) metal-induced surface-charge-transfer (SCT) detectors, (Wi et al., Appl. Phys. Lett., 2015, 107, (6)) as illustrated in FIG. 11 are developed.

Optimal operation conditions of $MoS_2$ photodetectors: Integrated arrays of the above-described devices are produced and the optimal photodetector structure that is the most suitable for large-area bio-assay applications, in terms of detector-to-detector variations in optical responsivity (photocurrent per incident light power), quantum efficiency (number of photo-generated carriers/number of incident photons), and photocurrent noise level (time-dependent fluctuation of the photocurrent measured at a given illumination condition) is selected.

Figure 12:
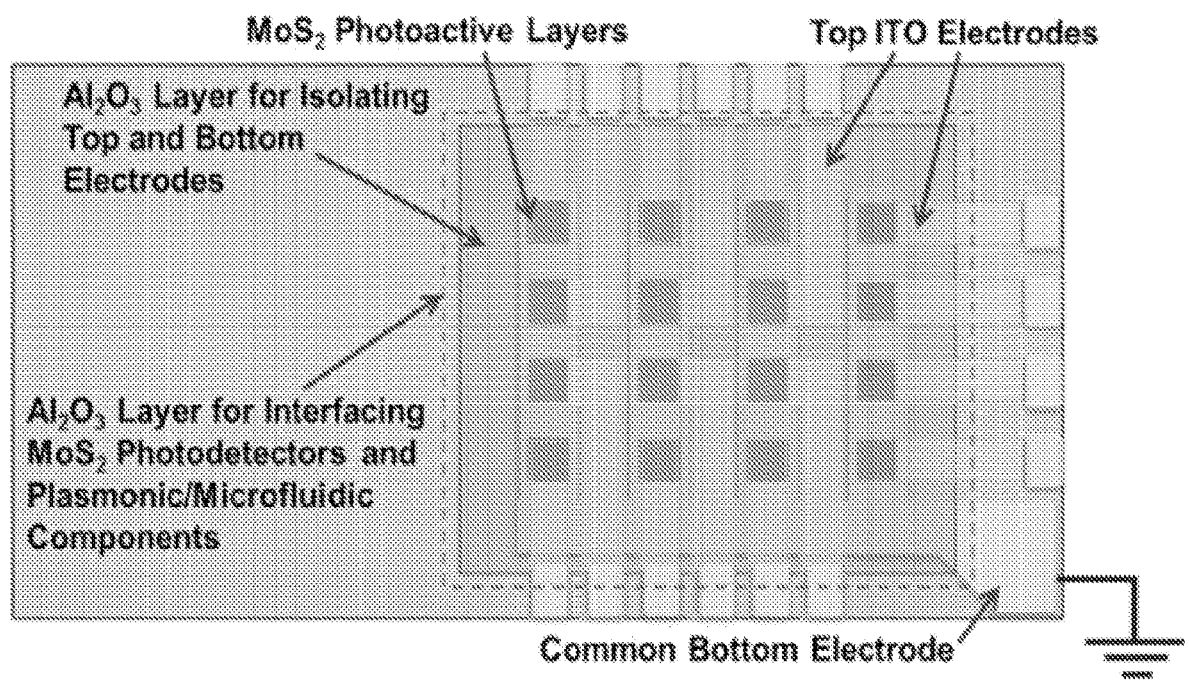
FIG. 12 shows a circuit layout including a set of finger contacts, which can realize addressable access to different MoS$_2$ photodetectors arranged in a 4×4 array.

$MoS_2$ photodetector arrays with an integrated signal readout circuit: To enable fast addressable reading of the photocurrent signals from different detectors in an array, the circuit illustrated in FIG. 12, which includes a set of independent finger contacts and is used to realize the access to a 4×4 array of photodetectors. When the $MoS_2$ device layer is assembled with the nanoplasmonic optical filter layer, each photodetector array is aligned with each biosensor array on the optical filter layer for multiplexed detection. For the salivary cytokine biosensor platform, such a 4×4 photodetector array is sufficient for obtaining the concentration profiles of critical cytokines. Optionally, if a larger sensor array is demanded for other specific bioassay applications, $MoS_2$ photodetectors are integrated onto a commercially-available driving circuit of CMOS arrays, which can realize the random access to large sensor arrays.

Plasmonic nanoantenna biosensor structure synthesis method: High-density plasmonic nanoantenna arrays are constructed on a flexible substrate with good uniformity and stability by extending the nanomaterial synthesis technique described above. The methods employed here are a manufacturing process combining nano building block self-assembly and chemical over growth. Specifically, high-density plasmonic nano antenna arrays with a structural order, an optimized interparticle distance, and desirable sub-nano features are developed; flexible plasmonic substrate are made; and the arrangement and order of the plasmonic nano antenna arrays are characterized.

Uniform plasmonic nano antenna arrays: Achieving high density, structural uniformity, and stability all together utilizes optimization of both the adhesion to the substrate and satellite sub-nano features. A self-assembly technique using nano building blocks, which serve as molecular units made of block-copolymer (structure directing molecule) and metal ion (metal precursor for plasmonic structure) are used. In this method, ordered nano building block is formed from a poly (styrene)-b-poly (2-vinylpyridine) and gold precursor. A thin film of the self-assembled nano building blocks is prepared by spin coating. High power plasma treatment (W=100 W) is followed by reduction of the metal contents in and removal of the organic component of the block copolymer from the self-assembled building blocks. The block-copolymer concentration and the surface charge intensity is varied as control parameters to optimize the adhesion between the formed plasmonic nano antenna arrays and the substrate (initially $SiO_2$ used). Then, the resulting nano antenna feature is contemplated to be highly ordered and uniform as. Secondly, to ensure that the plasmonic nano antenna yields high sensitivity to surface biomolecular the satellite sub-nano features are optimized by using the chemical overgrowth method. The silver ion concentration is varied from 0.001M to 0.1M in chemical reaction. Subsequently, the morphology of the nano antenna arrays is characterized by using scanning electron microscopy (SEM). The LSPR property is analyzed by dark field microscopy and optical spectroscopy. The effect of block-copolymer and silver ion concentrations on the size distribution and extinction spectrum of the constructed nano antenna is quantified. Five samples for each synthesis condition are prepared to study repeatability of the structure.

Flexible plasmonic substrate: Plasmonic nano antenna arrays were made on a flexible substrate by maximizing the physical interaction between the nano building blocks and the flexible substrate. As the flexible substrate, PDMS is used because of its ease of fabrication, high optical transmittance and high mechanical stability. After preparing a thin PDMS film (L×W×H=1 cm×1 cm×500 μm) by spin coating, the surface treatment of flexible substrate is followed by using $O_2$ (or $CF_4$) plasma treatment and chemical treatment (sodium hydrogen oxide solution (NaOHaq) or hydrogen chloride solution (HClaq)) to form high density —COOH group on the surface of flexible substrate. These treatments yield a strong adhesion of the plasmonic nano antenna arrays to the PDMS substrate. The building block formation method described above coupled with $O_2$ plasma treatment is applied to construct the nano antennas on the PDMS substrate. This study optimizes the mechanical stability and optical response of the constructed nano antenna arrays under structural bending. For this purpose, multiple plasmonic nano antenna array-covered PDMS substrates are prepared under varying conditions (time, reagent concentration, and plasma power) of the surface treatment. The mechanical stability of these substrates is characterized using scanning electron microscopy (SEM) images at a given bending condition. At the same time, the surface density of the nano antenna structure is quantified. To study the optical property variation with θB, the spectral shift (Δλ) and scattering light intensity is measured as functions of θB using an optical spectrometer and a dark-field optical microscope (Nikon Eclipse Ti-S, Nikon, Japan) coupled with a single-photon electron multiplying charge-coupled detector (EMCCD) (Photometrics, Tucson, Ariz.).

Structural order and arrangement of plasmonic nano antennas: The local extinction and the electric field around the plasmonic nanoantenna structure as a function of particle diameter, interparticle distance and structural order (2D hexagonal and 2D rectangular array) is measured. Dark-field microscopy coupled with high-resolution optical spectroscopy and finite element analysis (FEA)-based EM field simulation is used. Results combined with the measured LSPR extinction peak and the calculated EM fields provide information that aids in optimizing the diffraction coupling and light confinement within the plasmonic nano antennas for high-sensitivity biosensing. In addition, the results are interpreted to estimate the density and intensity of hot spot with substrate bending.

Figure 13:
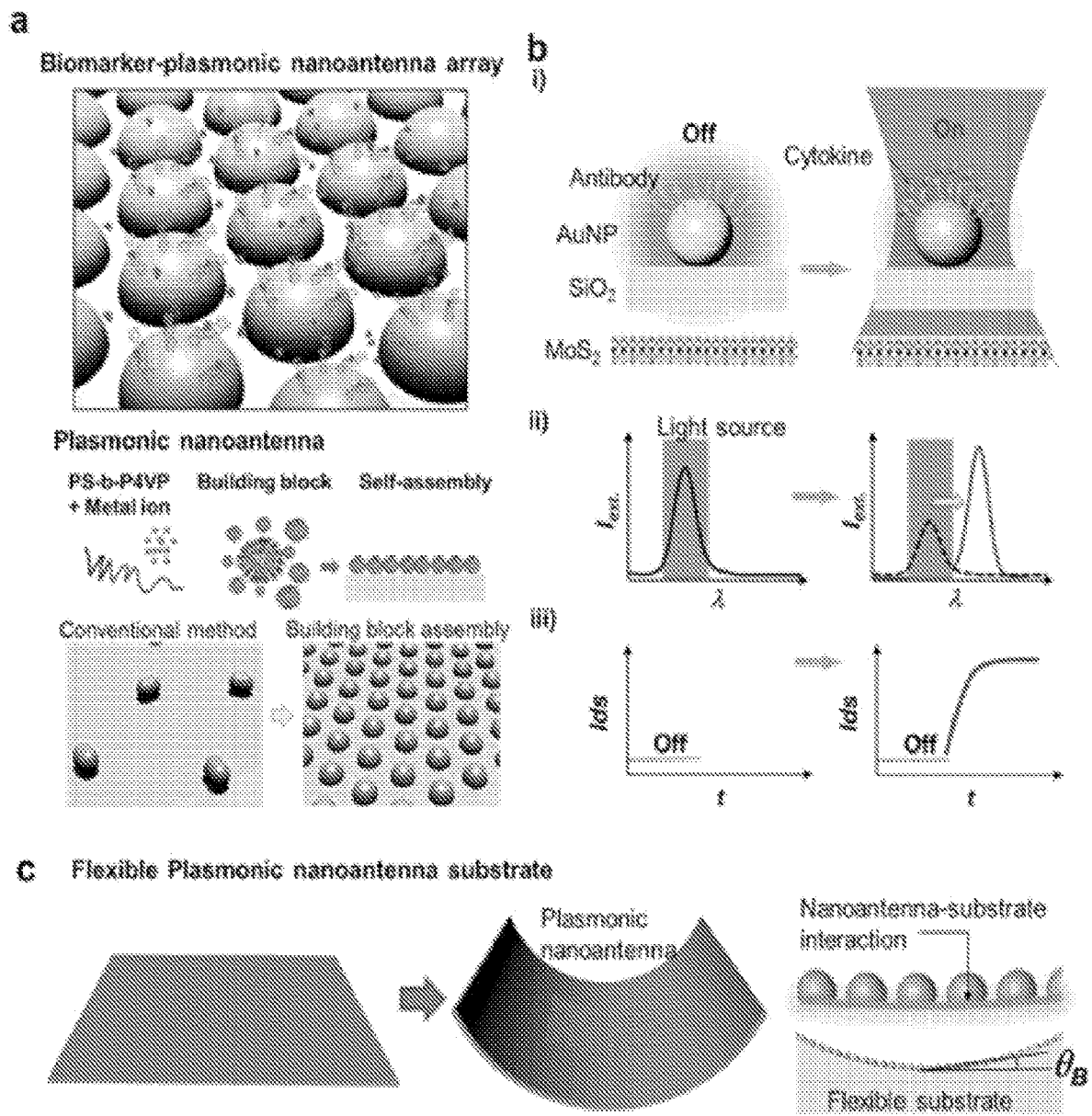
FIG. 13 shows protocols of biosensor synthesis for optimal performances (LOD, dynamic range, sampling-to-detection time. (a) receptor (antibody)-conjugated plasmonic nano antenna arrays, (b) integrated nano plasmonic optical filter on 2D MoS$_2$ photodetector for cytokine detection, and (c) flexible plasmonic nano antenna substrate by optimizing nano antenna-substrate adhesion.

Fully flexible plasmonic nanoantenna/$MoS_2$ salivary cytokine biosensor microsystem: A microfluidics-based fully flexible plasmonic nano antenna/$MoS_2$ salivary cytokine biosensor microsystem is built upon the key device components described above. A flexible microfluidic chip for multiplexed cytokine detection is shown in FIG. 13. There are primarily three factors determining the theoretical LOD and speed of a biosensing system: (1) inherent biosensor sensitivity towards analyte binding events; (2) affinity between target analytes and receptors; (3) sample delivery (Squires et al., Nature biotechnology, 2008, 26, (4), pp. 417-426). It is anticipated that the plasmonic nano structures with high structural uniformity, surface density, and satellite sub-nanometer branches leading to enhanced EM localization will further push down the LOD of the plasmo-nano-photoelectronic biosensor significantly below the 1.0 pg/mL level owing to the increased surface affinity between the nano structures and biorecognition sites (antibodies).

Using COMSOL multiphysics modeling, the dimensions of the microfluidic channels are designed to enhance the diffusion/convection-driven sample delivery to the sensing sites. This improves the sensor response speed. Four barcode-shaped patterns (~200 μm wide) of the plasmonic nano antenna arrays are lithographically fabricated on a PDMS substrate. These plasmonic sensor barcode patters are conjugated with antibodies targeting key salivary cytokines: 1L-β, IL-6, IL-8, and TNF-α respectively (FIG. 13b), by a microfluidic functionalization technique (Oh et al., ACS sensors, 2016, 1, (7), pp. 941-948; Chen et al., ACS nano, 2015, 9, (4), pp. 4173-4181) (FIG. 13c). After the biosensor conjugation process, a PDMS layer of microfluidic channels prepared by the conventional soft lithography technique is bonded to the plasmonic nano antenna array PDMS substrate with its surface treated by $O_2$ plasma (P=50 W). This layer assembly results in sensor barcode patterns orthogonal to 4 sample detection flow channels (FIG. 13a). The PDMS microfluidic layer has a region close to the inlet that has a sample loading channel with micro pillar structures. These pillar structures filter out salivary constituents potentially causing error to the downstream measurement, such as mucus, white blood cells, and epithelial cells. The cytokine sample uptake is done by means of passive biofluidic motion. Here, a degassing process developed by Park (Kokalj et al., Lab on a Chip, 2014, 14, (22), pp. 4329-4333) is used to drive the biofluidic motion in the PDMS-based microfluidic chip (FIG. 13). The porous structure of PDMS allows air in the originally empty PDMS channels to be pulled out in a vacuum chamber. After the degassing process, a negative pressure is formed inside the PDMS channel. This negative pressure pulls the loaded sample fluid to the detection flow channels on the chip. Any electrical and mechanical components for the biofluidic motion are not necessary in the integrated microsystem.

As such, the constructed microfluidic biosensor device is expected to yield excellent sample handling capability with the passive fluidic manipulation mechanism. Such simple, yet powerful sample handling facilitates point-of-care device operation under limited resources.

After loading a test sample at 5 different concentrations (from 0.1 pg/mL to 1000 pg/mL) of target cytokines (1L-β, IL-6, IL-8, and TNF-α) suspended in a commercially available synthetic (artificial) saliva solution (Pickering Laboratories Inc., Mountain View, Calif.), dark-field images of the barcode-shaped biosensors are taken using a scanning optical microscopy setup with a motorized X-Y stage (ProScanIII, Prior Scientific, Rockland, Mass.). A band pass filter is used to capture the maximum biosensor scattering light intensity variation resulting from the LSPR shift during analyte surface binding. The images are captured with the above-described EMCCD camera and recorded using NIS-Element BR analysis software. A customized Matlab code is used to analyze and quantify the scattering intensity shift for each biosensor pattern. The region of interest (ROI) is automatically selected during the image scanning process through an edge detection/background subtraction algorithm, and then the raw data of each pixel is read out and processed. The scanned images are used to obtain calibration standard curves for the biosensors across the entire microchambers and compared to each other. To develop statistical confidence for the device performance repeatability, 5 devices are tested with the same test sample and the analysis of variance (ANOVA) is used to determine the overall sensor performance variation across the devices. To the end, the validated microfluidic device is ready to be integrated for a fully flexible plasmonic nanoantenna/$MoS_2$ salivary cytokine biosensor device.

In some embodiments, antibodies are replaced with cytokine targeting aptamers (synthetic oligonucleotide molecules) as the sensor receptors. Upon the binding of the target cytokine molecules, the aptamers experience conformational changes, which translates to highly amplified LSPR spectral peak shifts leading strong signal changes. These signal changes are highly specific to the surface binding of the target analytes.

Figure 14:
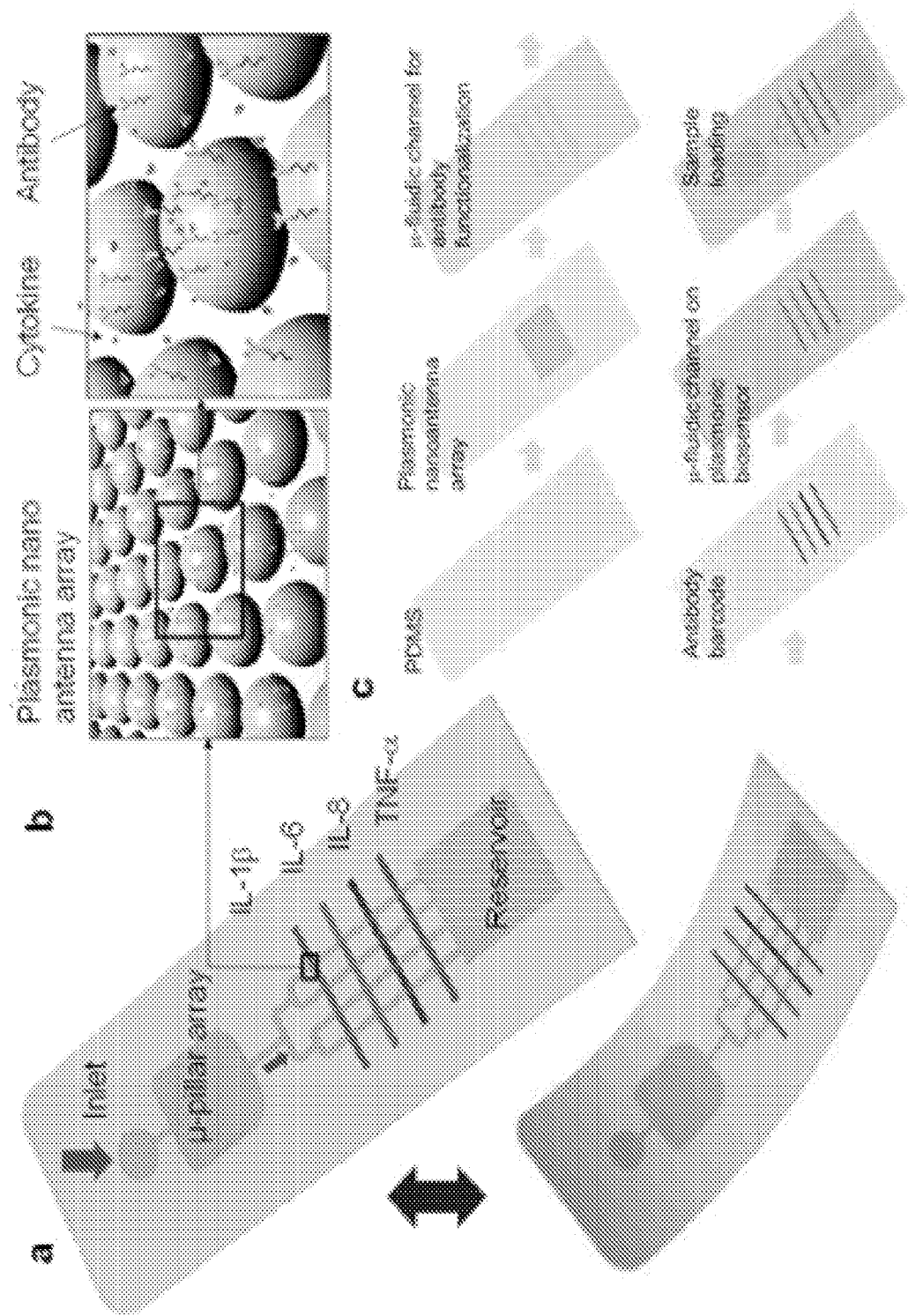
FIG. 14 shows construction of flexible microfluidic chip with multiplexed plasmonic nanoantenna biosensors. a) flexible chip design; b) integrated plasmonic nano biosensor on flexible PDMS substrate; c) fabrication step.
Figure 15:
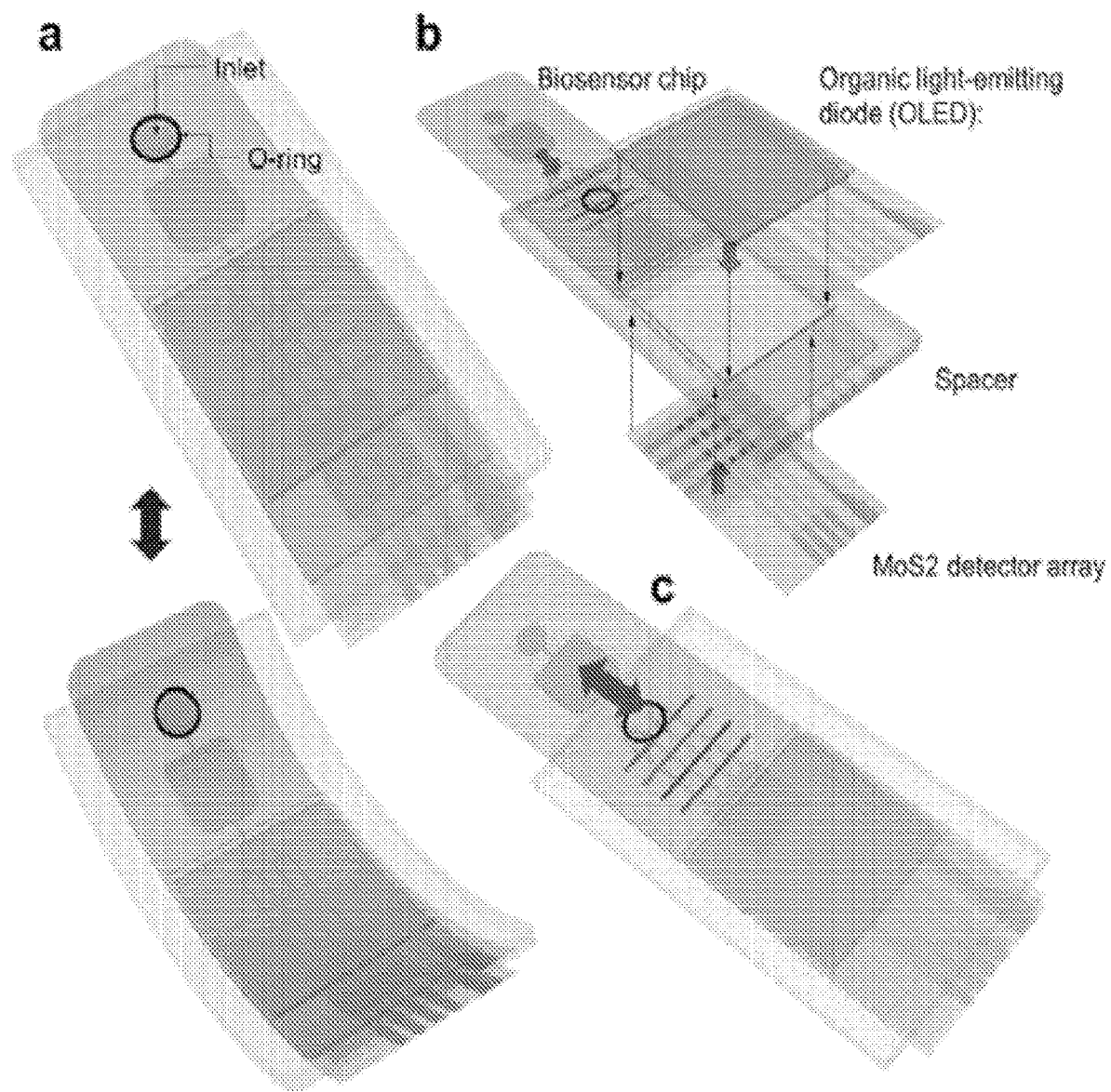
FIG. 15 shows a schematic of fully flexible plasmonic nano antenna/MoS$_2$ salivary cytokine biosensor microsystem. (a) device design; (b) integration scheme; (c) dischargeable biochip from the microsystem device.

$MoS_2$ salivary cytokine biosensor microsystem: The system includes 4 parts: (1) an off-the-shelf light source layer (Organic light emit diode (OLED); e.g., Crystalfontz); (2) a plasmonic biosensor chip; (3) a 2D $MoS_2$ photo detector layer with integrated signal readout circuits; and (4) a body frame serving as a cartridge spacer to fix the position of each layer (FIG. 14). The cartridge arrangement allows for replacement of the chip after the measurement. This permits repeated use of the $MoS_2$ photodectors and the OLED. The O-ring above the microfluidic intel ensures good hermetic sealing of fluid. The entire microsystem is assembled such that the flow channels illuminated by the overhead OLED are aligned with the underneath $MoS_2$ photodetector arrays. To achieve reliable optical signal reading, the structural alignment between the OLED light source, the biosensors (antibody-conjugated plasmonic nano antenna patterns), and the $MoS_2$ layer (detector) is consistent even under bending. The spacer (body frame) is to fix the distances between the OLED layer, the flexible biosensor microfluidic chip, and the flexible 2D MoS$_2$ detector array substrate. The OLED and a flexible MoS$_2$ are attached onto the empty areas of the top and bottom surfaces of the spacer, respectively. Then, after the operation of the microfluidic chip, a new chip can readily replace it for new next measurements. For light illumination and signal transmission, the OLED light source is connected via an electrical wire to an off-chip computer system and the photo response in the MoS$_2$ detector is measured by using a semiconductor parameter analyzer (HP).

A specific wavelength of the OLED light induces the LSPR effect to the plasmonic nano antenna surfaces in the biosensor microfluidic chip. A designated code in a personal computer control light illumination conditions. A sample of artificial saliva (<10 µL in volume) spiked by the target cytokines of known concentrations is introduced to the inlet of the biosensor system and the time-course variation of the photocurrent (IDS) of the MoS$_2$ detector is measured. In addition, all the photocurrent IDS is measured against voltage (VDS) for the MoS$_2$ detector arrays using a semiconductor parameter analyzer (HP). The obtained IDS-VDS curves are systematically processed using Matlab. All the measurements will be repeated at θB varying from 0° to 30°. The overall LOD, sensing dynamic range, and selectivity of the whole system is obtained as a function of θB. This study measures IDS at cytokine concentrations varying from 0.1 pg/mL to 100 ng/mL over to obtain both analyte binding curves and standard curves for the 4 target cytokines (1L-β, IL-6, IL-8, and TNF-α). The obtained binding curves provide the time constant (sampling-to-answer) of the biosensors while the standard curves will allow for estimating the LOD of the system, which is given by $3\sigma/K_{slope}$, where σ and $K_{slope}$ are the standard deviation of background signal obtained from a blank control and the regression slope of each standard curve, respectively.

Additionally, to test the biosensor selectivity, a mixture of the target cytokines with 5 different concentrations (from 0.1 pg/mL to 100 ng/mL) is prepared, and cross-talk across the 4 biosensor patters is characterized. This cross-talk is expected to be very small for plasmonic nano antenna structures previous study (Chen et al., ACS Nano, 2015, 9, (9), pp. 8773-8785). The LOD of the whole device is determined by both the optical property of the plasmonic nano structures and the photoelectric property of the MoS$_2$ photodetector. A LOD<1.0 pg/mL and a response time<10 min is expected.

Figure 16:
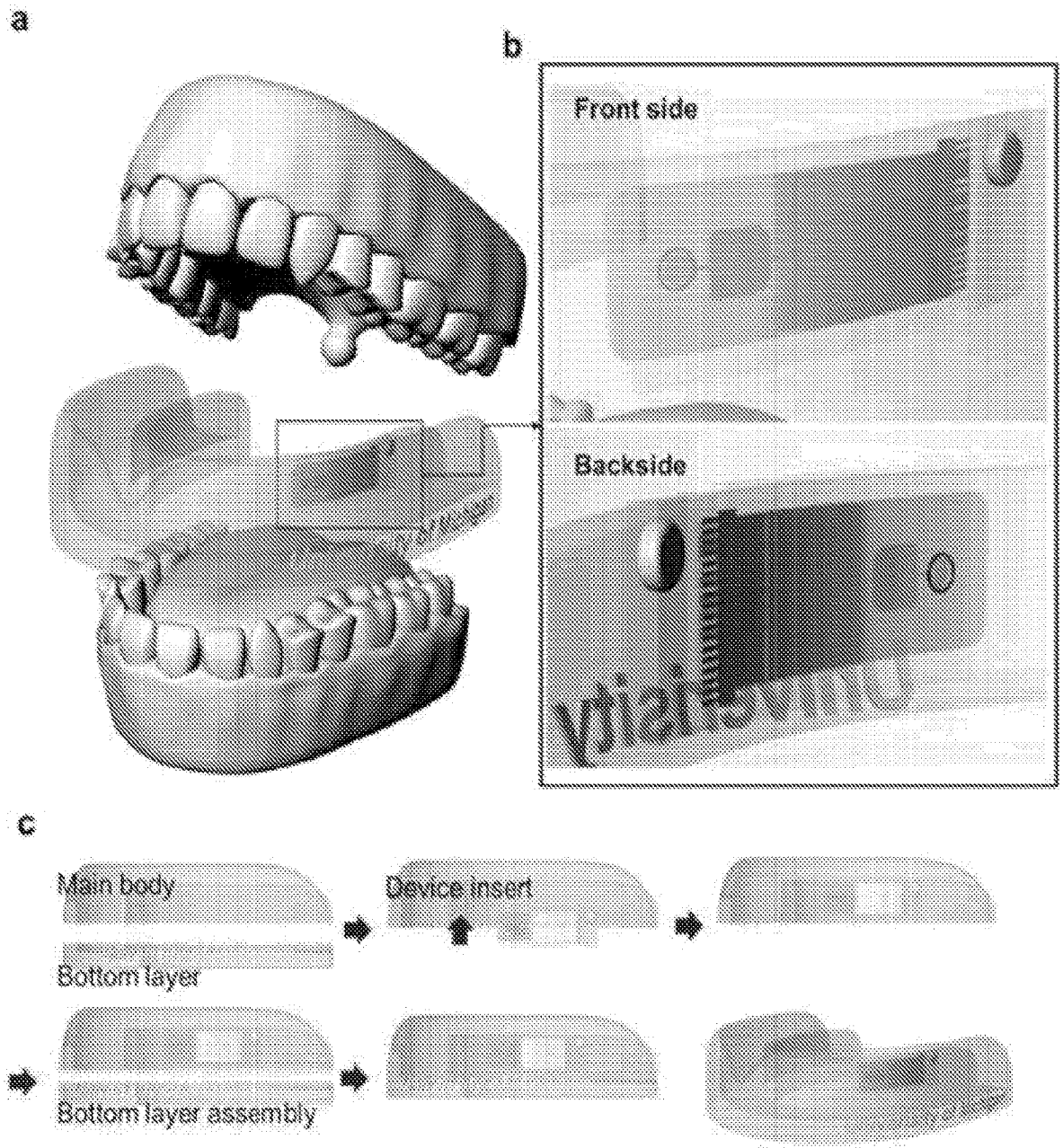
FIG. 16 shows a biosensor platform on a curved surface as a mouth guard type sensor. a) Schematics; b) A curved device inside of the mouth guard; c) Assembly process.

Operation of the biosensor microsystem on a curved surface: Although a number of wearable biosensors have been used in biomedical monitoring for a decade, any fully integrated system for cytokine detection-based immune system monitoring has not been reported. A mouth guard structure including two parts: a curved main body and a bottom layer is constructed. In the curved main body, the fully flexible plasmonic nano antenna/MoS$_2$ salivary cytokine biosensor microsystem is mounted inside the mouth guard with a signal wire connecting the on-chip circuit to an off-chip lab computer (FIGS. 16 a & b). The sample inlet of the mouth guard is connected to an inlet of the flexible biosensor device. When an artificial salivary sample is loaded into the inlet of the mouth guard, the sample is taken into the biosensor chip due to the negative pressure built up in the chip by the degas process described above. To filter out unnecessary macro debris in the sample, a polytetrafluoroethylene (PTFE) membrane (3 mm in diameter) is placed between the inlets of the mouth guard and the device. An O ring structure is placed inside the surface of the mouth guard to ensure a good sealing between the two inlets. After mounting the flexible biosensor device, the whole mouth guard structure is assembled to protect its inside (FIG. 16c). The whole mouth guard structure, including its inside geometry and inlet, is designed by 3D computer aided design to fit it to a structure mimicking typical human teeth. The integrated mouth guard structure is generated using a 3D printer machine. Considering biocompatibility, ethylene-vinyl acetate (EVA) is used as the structural material of the mouth guard. After loading the artificial saliva sample in the inlet of the mouth guard, the sample flow distribution in the biosensor chip is visualized using a food dye (green color). The transparency of the EVA-based mouth guard provides optical access to the device and enables one to observe the flow distribution with an optical microscope. By changing the volume of the colored artificial salivary sample, the minimum sample volume requirement is estimated. To establish statistical confidence, the test is repeated 10 times by prepare ring multiple mouth guard samples.

Having constructed the fully integrated the mouth guard and performed the salivary sample loading test, the operation of the biosensor platform under the condition mimicking a wearable point of-care disease monitoring setting is demonstrated. To test the performance of the microsystem, the fully flexible plasmonic nanoantenna/MoS$_2$ salivary cytokine biosensor chip is inserted into the cartridge spacer with which the OLED and the flexible MoS$_2$ layer are assembled. IDS change of the MoS$_2$ detector arrays, each assigned to detect one of the 4 target cytokines is measured as described above. The measurements described above are repeated to evaluate the LOD, dynamic range, speed, and specificity of the system. Using 10 units of the mouth guard, the replicable performance is confirmed. All the characterized sensor performances (e.g., LOD, dynamic range, speed, and selectivity are compared with results in above to validate reliable operation of the wearable mouth guard cytokine sensing system.

All publications and patents mentioned in the present application are herein incorporated by reference. Various modification and variation of the described methods and compositions of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled in the relevant fields are intended to be within the scope of the following claims.

We claim:

1. A localized surface plasmon resonance device (LSPR), comprising:
   A nanoplasmonic filter comprising an array of metallic nanoparticles comprising antigen-specific binding molecules specific for at least one analyte on an optically transparent dielectric layer; and a photoconductive flake layer comprising a few-layer MoS$_2$ layer, wherein said nanoplasmonic filter and said photoconductive flake layer are separated by a 100-300 µm deep air space.

2. The device of claim 1, wherein said air space is 170 µm deep.

3. The device of claim 1, wherein said metallic nanoparticles particles are gold nanoparticles or gold rods.

4. The device of claim 1, wherein said dielectric layer SiO$_2$.

5. The device of claim 1, wherein said MoS$_2$ layer is 15-20 nm thick.

6. The device of claim 1, wherein said analytes are cytokines, proteins, antibodies, or nucleic acids.

7. The device of claim 6, wherein said cytokines are selected from the group consisting of interleukin-1β(IL-1β), interleukin-2 (IL-2); interleukin-4 (IL-4); interleukin-6 (IL-6); interleukin-8 (IL-8); interleukin-10 (IL-10); interleukin-12 (IL-12); interferon-gamma (IFN-γ); and tumor-necrosis-factor alpha (TNF-α).

8. The device of claim 1, wherein said device comprises a substrate.

9. The device of claim 8, wherein said substrate is glass or thermoplastic.

10. The device of claim 8, wherein said substrate is flexible.

11. The device of claim 1, wherein said device further comprises a plurality of microfluidic channels in communication with said nanoplasmonic filter.

12. The device of claim 11, wherein said device comprises an inlet in operable communication with said microfluidic channels.

13. The device of claim 11, wherein said device further comprises a sample loading channel with micro pillar structures in operable communication with said inlet and said microfluidic channels.

14. A system, comprising:
a) the device of claim 1; and
b) a LSPR detection apparatus.

15. The system of claim 14, wherein said system further comprises one or more of a sample handling component, a data analysis component, and a user interface.

16. A method of measuring levels of one or more polypeptides, comprising:
a) contacting the device of claim 1 with a sample; and
b) measuring the level of one or more polypeptides in said sample using LSPR.

17. The method of claim 16, wherein method is performed in 10 minutes or less.

18. The method of claim 16, wherein said method has a limit of detection of 20 fM or lower.

* * * * *